(12) United States Patent
Aulet et al.

(10) Patent No.: US 11,850,470 B2
(45) Date of Patent: Dec. 26, 2023

(54) SYSTEM AND METHOD FOR IMPROVING CARDIO MACHINE CAPABILITIES BY DYNAMICALLY ADAPTING WORKOUTS TO AN ATHLETE

(71) Applicant: Ergatta, Inc., Brooklyn, NY (US)

(72) Inventors: Thomas Aulet, Brooklyn, NY (US); Alessandra Gotbaum, Brooklyn, NY (US); Prasanna Swaminathan, Robbinsville, NJ (US)

(73) Assignee: Ergatta, Inc., Brooklyn, NY (US)

( * ) Notice: Subject to any disclaimer, the term of this patent is extended or adjusted under 35 U.S.C. 154(b) by 146 days.

(21) Appl. No.: 17/390,621

(22) Filed: Jul. 30, 2021

(65) Prior Publication Data
US 2022/0032125 A1    Feb. 3, 2022

Related U.S. Application Data

(60) Provisional application No. 63/059,760, filed on Jul. 31, 2020.

(51) Int. Cl.
*A63B 24/00*     (2006.01)
*A63B 22/00*     (2006.01)
*A63B 71/06*     (2006.01)

(52) U.S. Cl.
CPC ...... *A63B 24/0006* (2013.01); *A63B 22/0076* (2013.01); *A63B 24/0062* (2013.01);
(Continued)

(58) Field of Classification Search
CPC ............ A63B 24/0006; A63B 22/0076; A63B 24/0062; A63B 24/0075; A63B 71/0622;
(Continued)

(56) References Cited

U.S. PATENT DOCUMENTS

| 6,902,513 B1 | 6/2005 | McClure |
| 10,065,074 B1 | 9/2018 | Hoang |

(Continued)

FOREIGN PATENT DOCUMENTS

| RU | 2520404 C1 | 6/2014 | |
| WO | WO-2011105914 A1 * | 9/2011 | ........... A61B 5/0022 |
| WO | 2019221933 A1 | 11/2019 | |

OTHER PUBLICATIONS

International Search Report and Written Opinion dated Nov. 3, 2021, Patent Application No. PCT/US2021/044075, 10 pages.

*Primary Examiner* — Sundhara M Ganesan
*Assistant Examiner* — Jacqueline N Loberiza
(74) *Attorney, Agent, or Firm* — Davis Wright Tremaine LLP

(57) ABSTRACT

Systems and methods are described for personalizing a fitness or workout plan based on an athletes past performance. In some aspects, performance metrics from at least two workout sessions performed by a user using exercise equipment, may be obtained, where each workout session includes a plurality of intervals corresponding to one of a number of different intensity levels. The performance metrics over a subset of the intervals may be compared with a prescribed performance of the corresponding interval to generate interval comparisons. Using the interval comparisons, at least one of a length or an intensity level of at least one interval of a future workout session may be modified.

21 Claims, 15 Drawing Sheets

(52) U.S. Cl.
CPC ...... *A63B 24/0075* (2013.01); *A63B 71/0622* (2013.01); *A63B 2024/0015* (2013.01); *A63B 2024/0065* (2013.01); *A63B 2024/0068* (2013.01); *A63B 2230/75* (2013.01)

(58) Field of Classification Search
CPC .... A63B 2024/0015; A63B 2024/0065; A63B 2024/0068; A63B 2230/75
See application file for complete search history.

(56) References Cited

U.S. PATENT DOCUMENTS

| | | |
|---|---|---|
| 10,886,016 B2 | 1/2021 | Ohnemus et al. |
| 11,130,017 B2 | 9/2021 | Smith et al. |
| 2010/0248901 A1 | 9/2010 | Martens |
| 2011/0040193 A1 | 2/2011 | Seppanen et al. |
| 2021/0008413 A1* | 1/2021 | Asikainen ............. G06F 3/0304 |

* cited by examiner

Your Intensity Zones

| 3:00 | 2:45 | 2:44 | 2:31 | 2:35 | 2:03 | 2:02 |
|---|---|---|---|---|---|---|
| PADDLE 302 | | STEADY 304 | | RACE 306 | | SPRINT 308 |
| Approx. 55-75% Effort | | Approx. 75-85 Effort | | Approx. 85-95% Effort | | Approx. 100% Effort |
| Low intensity. Easy to breathe. Good for warm-up, recovery, and cool-down. | | Moderate intensity. Heavier breathing, can maintain a conversation. | | Aggressive intensity. Heavy breathing, hard time talking | | Max intensity. Hard to breathe, cannot talk. |

RECALIBRATE | FINISHED

FIG. 3

| Metric | Change | Expected Power Multiplier |
|---|---|---|
| Rest between sessions | ↑ | ↑ |
| Session duration | ↑ | ↓ |
| Interval duration | ↑ | ↓ |
| Ratio of time at higher intensities | ↑ | ↓ |
| Average heart rate | ↑ | ↑ |

| Date | I1 Actual/Exp | I2 Actual/Exp |
|---|---|---|
| 1/1 | 100m@85%/<br>100m@85% | 1,500m@75%/<br>2,000m@85% |
| 1/3 | 105m@85% | 1,500m@77% |
| 1/6 | 100m@85% | 1,500m@75% |
| 1/8 | 120m@65% | 1,750m@85% |
| 1/11 | 70m@65% | 1,300m@60% |
| 1/13 | 100m@85% | 1,600m@77% |
| 1/16 | 105m@85% | 1,650m@78% |
| 1/19 | 110m@85% | 1,700m@79% |
| 1/21 | 120m@90% | 1,800m@80% |
| 1/23 | 125m@90% | 1,850m@80% |

FIG. 11

SYSTEM AND METHOD FOR IMPROVING CARDIO MACHINE CAPABILITIES BY DYNAMICALLY ADAPTING WORKOUTS TO AN ATHLETE

CROSS-REFERENCE TO RELATED APPLICATIONS

This application claims the benefit of U.S. Provisional Patent Application No. 63/059,760, filed Jul. 31, 2020, titled "SYSTEM AND METHOD FOR IMPROVING CARDIO MACHINE CAPABILITIES BY DYNAMICALLY ADAPTING WORKOUTS TO THE ATHLETE AND PROVIDING FUNCTIONALITY TO RACE OTHER ATHLETES ASYNCHRONOUSLY" and co-pending U.S. patent application Ser. No. 17/390,34, titled "SYSTEM AND METHOD FOR PROVIDING FUNCTIONALITY TO RACE OTHER ATHLETES ASYNCHRONOUSLY", filed on Jul. 30, 2021, the disclosures of which are incorporated herein by reference in their entirety.

BACKGROUND

Currently, equipment used to train cardiovascular fitness (hereafter referred to as "cardio equipment") has limited options for content and programming. There is an emerging solution in streaming fitness classes, but that solution lacks personalization. Personalizing workouts can be desirable for effective programming. Personalizing in some examples can include one or a combination of: tailoring a workout to a user's specific fitness profile, providing quantifiable goals based on that fitness profile, and/or adjusting the fitness profile as the user's fitness changes. Without these sorts of personalizations, current cardio equipment lacks the ability to provide effective programming. These sorts of equipment instead rely on subjective loads and prescriptions given to the user. Further, they rely on subjective measures of success based on relative intensity.

In view of the foregoing, a need exists for an improved system and method for specifying workout objectives and goals, measuring the achievement of those objectives, and adjusting future workout objectives and goals to elicit gains in fitness, in an effort to overcome the aforementioned obstacles and deficiencies of conventional cardio machine systems.

BRIEF DESCRIPTION OF THE DRAWINGS

Various techniques will be described with reference to the drawings, in which:

FIG. 3-5 illustrate example user interfaces representing a user's output relative to a number of intensity zones, in accordance with at least one embodiment;

FIGS. 7 and 8 illustrate example relationships between an expected power multiplier and various characteristics of workouts, in accordance with at least one embodiment;

FIG. 11 illustrates an example output from a series of workouts, in accordance with at least one embodiment;

DETAILED DESCRIPTION

Figure 1:
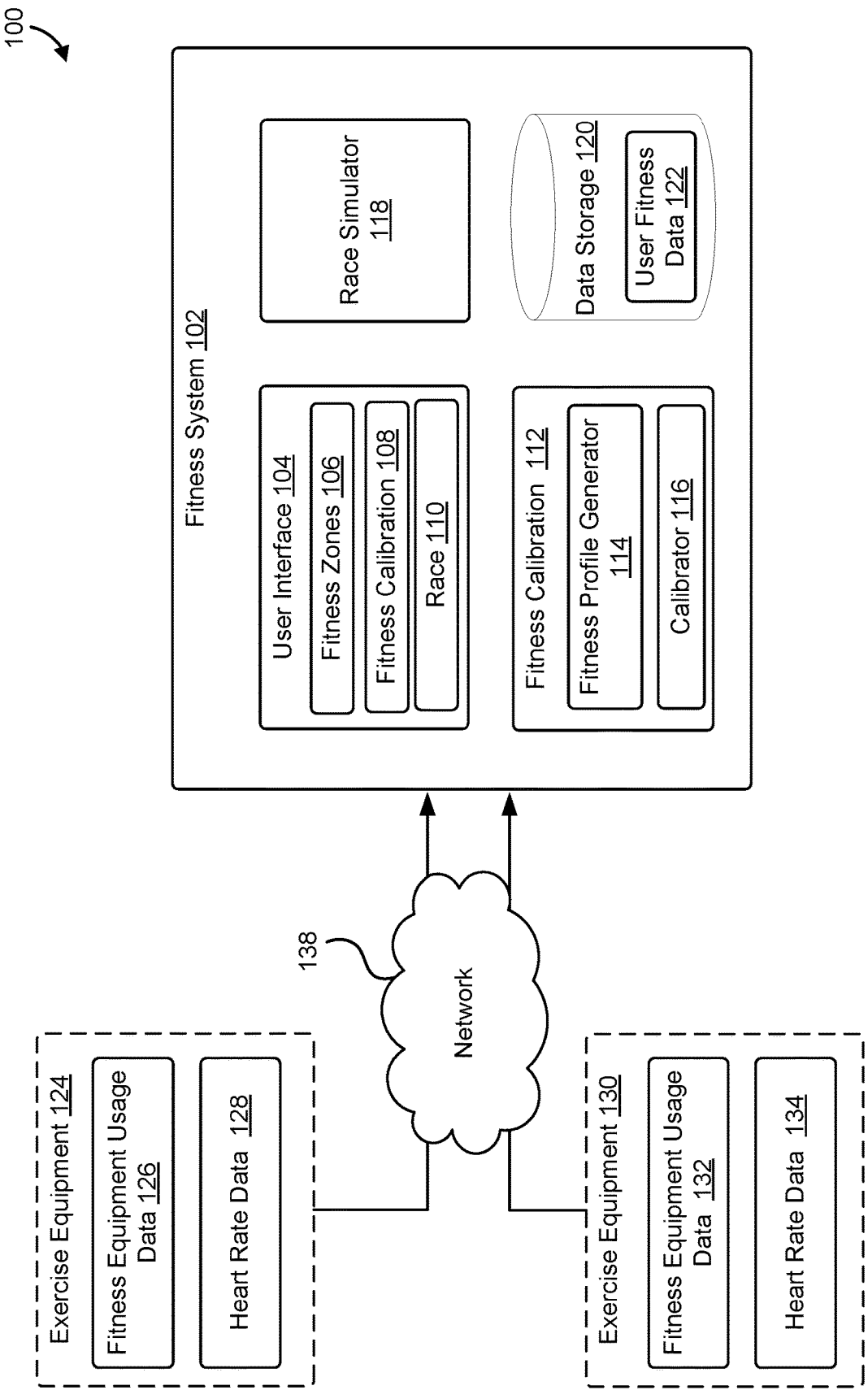
FIG. 1 illustrates an example of a fitness calibration system, in accordance with at least one embodiment.

Various embodiments of cardio machine systems and methods described herein are configured to create workouts that dynamically adapt intensity specifications to the user's fitness profile via a calibration, and/or adjust the fitness profile over time via detections of improvements or deteriorations in the user's general fitness. Some embodiments generate the user's fitness profile via a calibration. In other embodiments, a race simulation system may additionally or attentively be implemented to aid the user in optimizing training and motivation for training to achieve higher performance.

Workouts that dynamically adapt intensity specifications to the user's fitness profile via a calibration and adjust the fitness profile over time via detections of improvements or deteriorations in the user's general fitness can be desirable in various examples. Two issues have historically plagued many fitness machines: 1. workouts that specify intensities do not dynamically adjust to the user's fitness profile (except via unreliable user survey); and 2. devices do not detect whether or not there have been meaningful changes in the user's fitness that merit adjusting these. Accordingly, some preferred embodiments can include a method by which user's power- and endurance-fitness characteristics may be determined, via a calibration, and used to adjust the intensities prescribed to users to complete for each workout. Further, some preferred embodiments can include a method by which, as users' technical, power, and endurance qualities change over time, intensity prescriptions are adjusted accordingly.

In some aspects, a mechanism for evaluating a user's performance on exercise equipment by way of tracking a ratio of time spent within a sequenced array of varying intensity ranges may be provided. Measuring users' performance on exercise equipment has historically combined objective data (distance, time, speed), with subjective mechanisms for how a workout is supposed to feel. Some preferred embodiments can include a mechanism for evaluating a user's performance on exercise equipment by way of calculating a ratio of time spent within specific intensity zones, relative to a user's maximum intensity; and then by sequencing those measured zones into a structured workout and adapting the structured workout based on the user's performance during workout sessions.

In yet some aspects, a mechanism for linear representation of workout intensity objectives into visual zones is provided. Workout objectives are often presented with vague objectives around intensity; or they are presented as numerical objectives without comprehensive visual references. Some preferred embodiments can include a method to represent workout objective intensities as a linear set of visual zones, thereby providing more clarity and intuition around achieving these numerical objectives.

In some aspects, a mechanism for synchronizing races done at various times to a single race visual representation is provided. A desirable mechanism for group workouts in some examples is competition; yet, requiring users to be competing at the same time can be restrictive, especially for those who train at odd hours or in disparate time zones. Some preferred embodiments can include a method to synchronize races done at various times into a single race visual, thus providing a synchronous race with asynchronous competition. In some cases, a race interface may further econstruct one or more users' progression within a digital racing visual by interpolating sampled data-points along a digital race. In some cases providing a race interface may include dividing digital races performed on indoor cardio equipment into shorter individually ranked segments and accumulating segment complete times for an overall race time In the preceding and following description, various techniques are described. For purposes of explanation, specific configurations and details are set forth in order to provide a thorough understanding of possible ways of implementing the techniques. However, it will also be apparent that the techniques described below may be practiced in different configurations without the specific details. Furthermore, well-known features may be omitted or simplified to avoid obscuring the techniques being described.

As one skilled in the art will appreciate in light of this disclosure, certain embodiments may be capable of achieving certain advantages, including some or all of the following: 1) providing a more accurate and automatic adaption to a fitness workout or series of workouts based on recorded user performance; 2) providing a more intuitive user interface that quantifies and communicates effort in a linear way and representing a more readily understandable metric; and 3) providing a more robust simulated race interface, and other benefits and advantages that are described throughout this disclosure.

FIG. 1 illustrates an example environment 100 in which a fitness system 102 may be provided. In the example illustrated, a fitness system 102 may communicate with one or more pieces of exercise equipment 124, 130, over one or more networks 138. In some cases, the fitness calibration system 112 may be in whole or in part included with or co-located with exercise equipment 124, 130, such that an onboard screen and processing capabilities may be included with individual pieces of exercise equipment 124, 130. For example, a user interface 104 may be provided and displayed to a screen of an exercise equipment 124, 130. In other cases, user interface 104 may be provided to a mobile device or computing device of a user subscribed to a service that provides the fitness system 102.

As illustrated exercise equipment 124, 130 may generate fitness equipment usage data 126, 132, heart rate data 128, 134, and/or other performance metrics data (all referred to herein as performance data) that relates to user's output with respect to exercising with exercise equipment 124, 130. In some examples, exercise equipment 124, 130 may include a rowing machine, or device that simulates rowing in water. While the described systems and techniques will primary be described in terms of a rowing machine, it should be appreciated that the described systems and techniques may advantageously be adapted and applied to various different types of exercise equipment, including treadmills, stationary bicycles such as recumbent, spin and other various types of exercise bicycles, elliptical machines, stair stepping machines, climbing machines, Nordic training equipment, and even various forms of weight training equipment, such as cable actuated resistance machines. In any of these examples, the fitness equipment usage data 126, 132 generated may include any movement based information, such as speed, acceleration, power output, etc. Other performance metric data may include any data relating to a user's performance while using exercise equipment 124, 130, including any biometric data.

As illustrated, the fitness system 102 may include any number of computing devices, processors, memory, components, resources, etc., that operate to control and provide information relating to fitness equipment 124, 130. In some aspects, the fitness system 102 may include a fitness calibration subsystem 112 that may obtain data relating to a user's performance while using exercise equipment 124, 130, and use that information to generate a fitness profile for a user via a fitness profile generator 114 and calibrate one or more workout plans or fitness goals for the user via calibrator 116. In some cases, the fitness profile generator 114 and calibrator 116 may include processes executed by the fitness calibration subsystem 112. In one example, the fitness profile generator 114 may obtain biometric information relating to a user and performance data from one or more exercises or exercise routines performed by the user. The biometric information may include one or more attributes of the user, such as age, weight, height, gender, etc. The performance data may include power output, speed, heart rate and/or other information, such as any of fitness equipment usage data 126, 132, and heart rate data 128, 134, obtained during a workout or fitness test performed by the user using exercise equipment 124, 130. Using this information, the fitness profile generator may generate a fitness profile for the user. In some cases, the fitness profile may include a power output function or curve, such as power curve 200 discussed below in reference to FIG. 2. In some cases, the fitness profile generator 114 may also generate a map of different intensity zones for physical output for a given user, based on data obtained from exercise equipment 124, as will be described in greater detail below in reference to FIGS. 3-6.

In some aspects, the calibrator 116 may similarly obtain performance data from exercise equipment 124, 130 and use that information to adapt one or more fitness plans or sessions to better calibrate and personalize the workout to an individual user's performance and adaptations. In some cases, the output of the calibrator 116 may be used to modify one or fitness workout plans, such as may be stored in a data storage 120, as user fitness data 122. In some cases, data storage 120 may include any physical or virtual memory devices, including memory that is associated with or part of exercise equipment 124, 130 and/or memory that is separate from but in communication with exercise equipment 124, 130 and/or fitness calibration subsystem 112. Various calibration techniques will be described below in reference to FIGS. 7-13. User fitness data 122 may be separated into data relating to different users, such as fitness profile, fitness plan information, and/or performance metric for one or all fitness sessions engaged in by the user.

In some examples, the fitness system 102 may also include or provide a race simulator 118. In some aspects, the race simulator 118 may obtain performance data from exercise equipment 124, 130 corresponding to various users to then use that information to simulate a race during a current user's use of exercise equipment 124 or 130, such as to provide the user a better indication of progress or standing during a workout and/or to motivate the user to train harder. In some aspects, the data used to represent other users performing a similar workout to simulate a race may be obtained contemporaneously with a user performing the workout. This example may simulate a live race event, such that various users, such as in different locations, all perform the same or similar workout at the same time. In other cases, user performance data for a certain workout may be obtained and saved, such as via data storage 120, to then use that information at a later time to simulate a non-live race.

Figure 4:
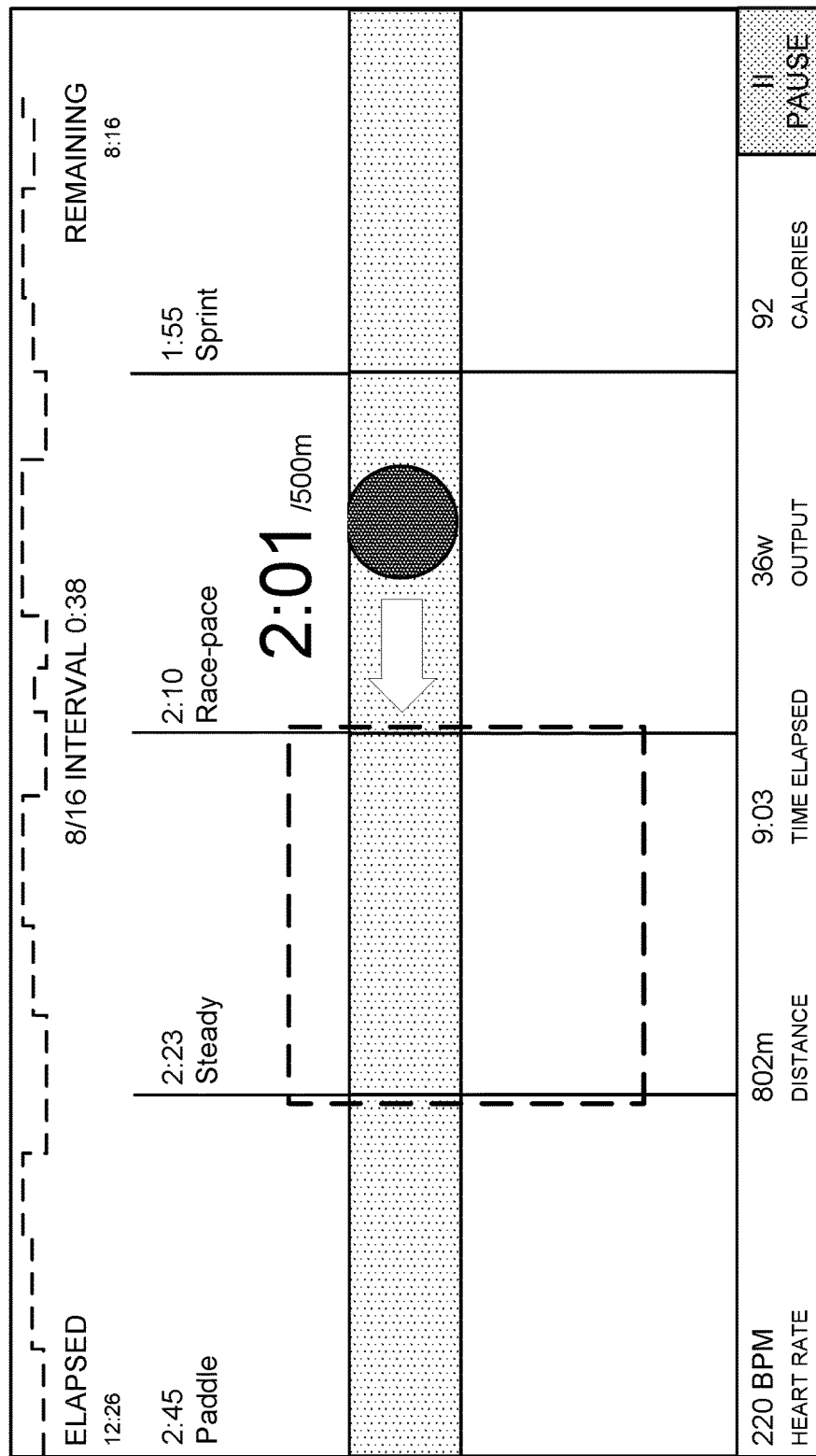
Figure 5:
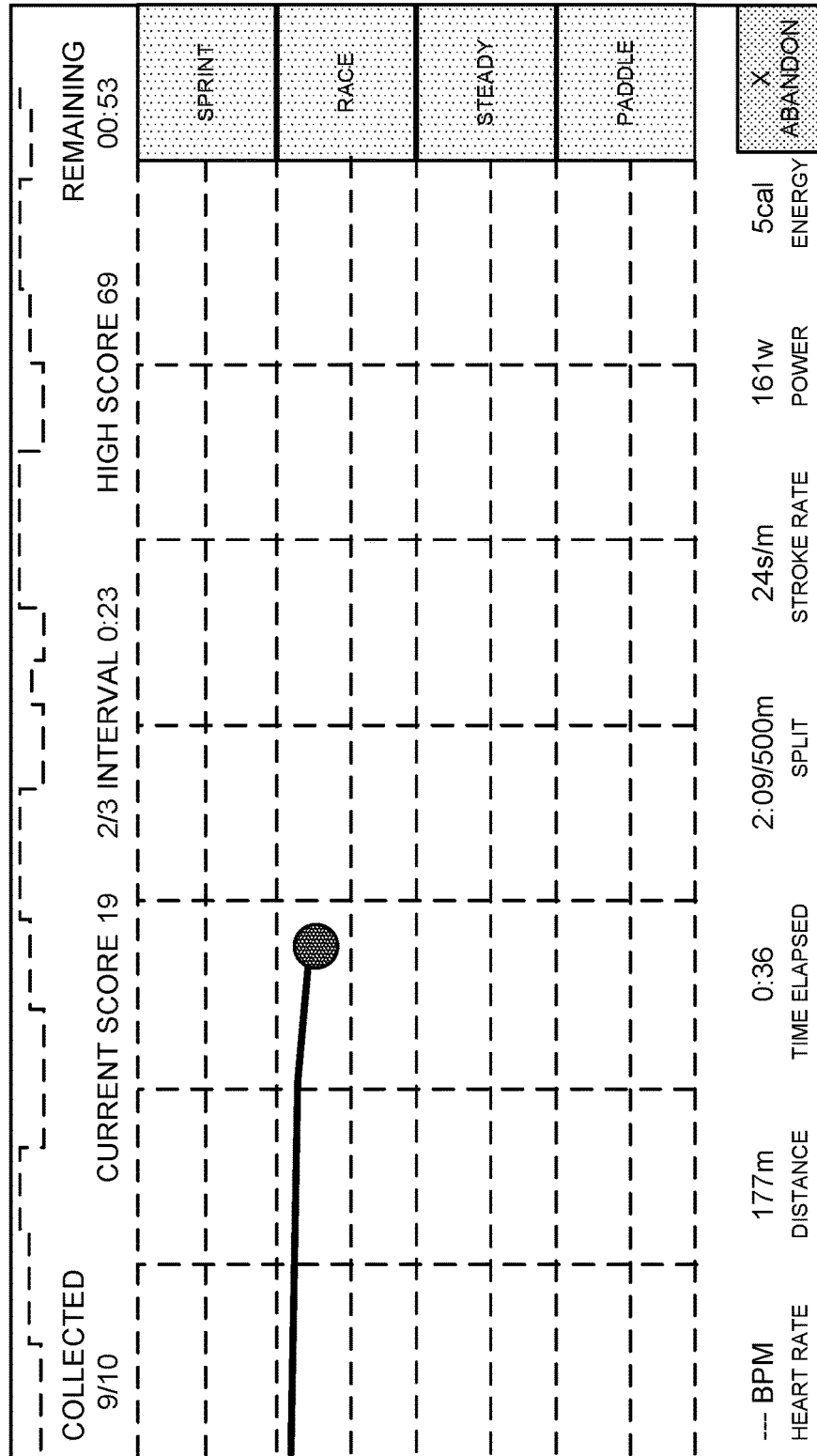
Figure 9:
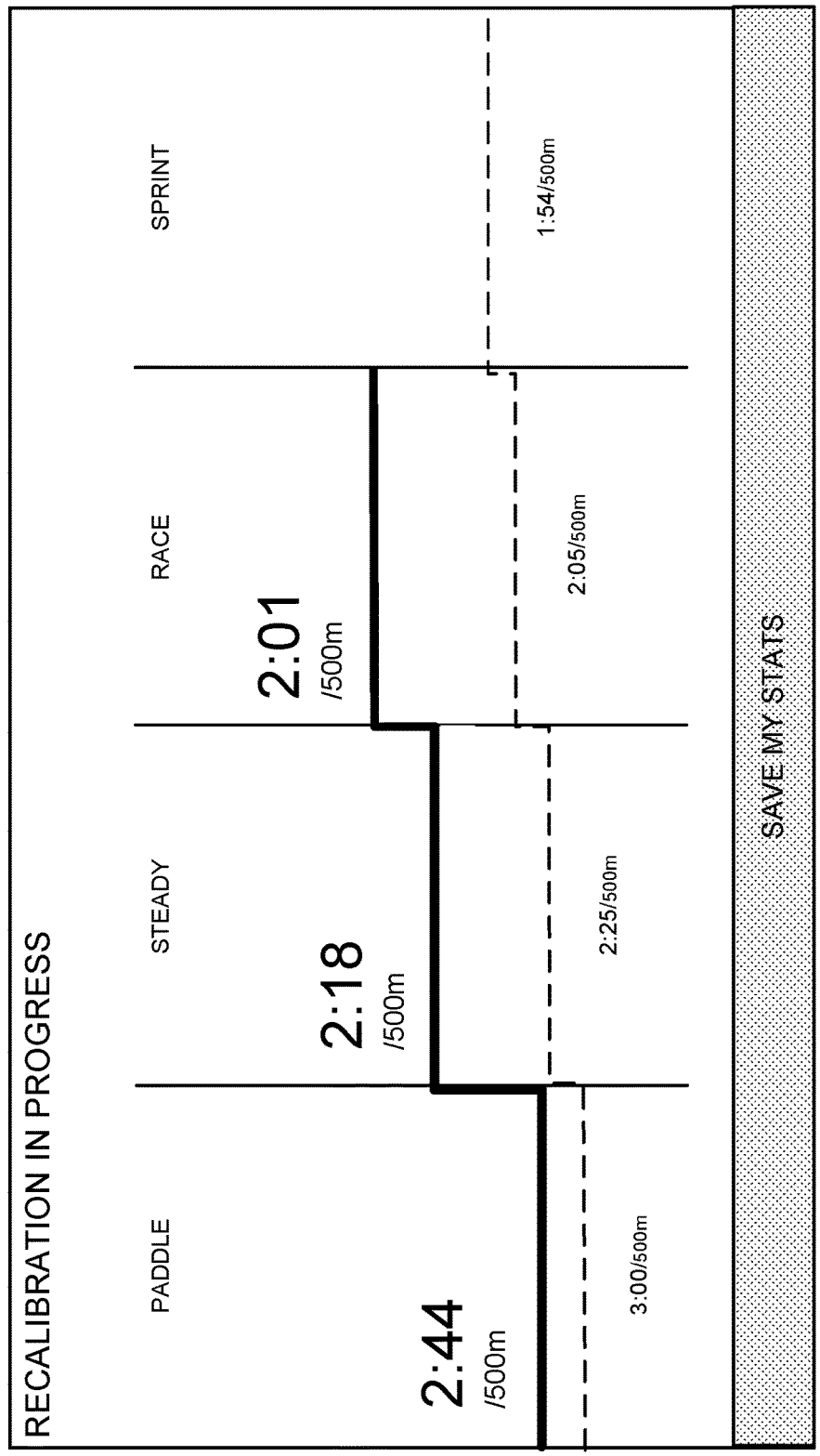
FIG. 9 illustrate an example user interface illustrating recalibration of a workout, in accordance with at least one embodiment.
Figure 15:
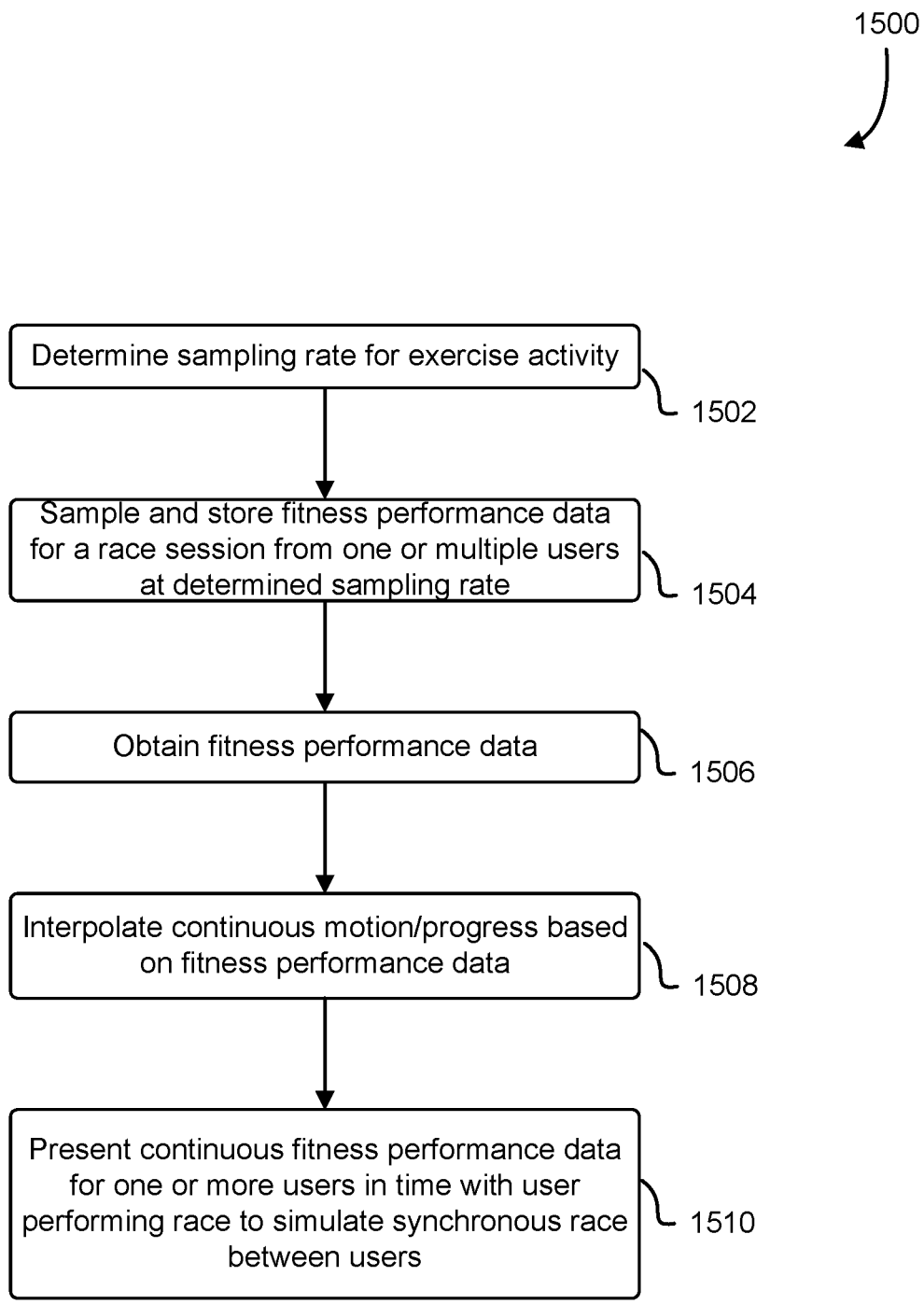
FIG. 15 illustrates an example process for providing a simulated race experience, in accordance with at least one embodiment.

In some aspects, the fitness system 102 may also provide one or more user interfaces 104, which may include a fitness zones component 106, a fitness calibration component 108, and a race component 110. Example representations of fitness zones, such as may be generated and provided by the fitness zones component 106, are illustrated in FIGS. 3-5. An example representation of fitness calibration, such as may be generated and provided by the fitness calibration component 108, is illustrated in FIG. 9, as will be discussed in more detail below. A representation of a fitness race, such as may be generated and provided by the race component 110, is illustrated in FIG. 15, as will be discussed in more detail below.

Figure 2:
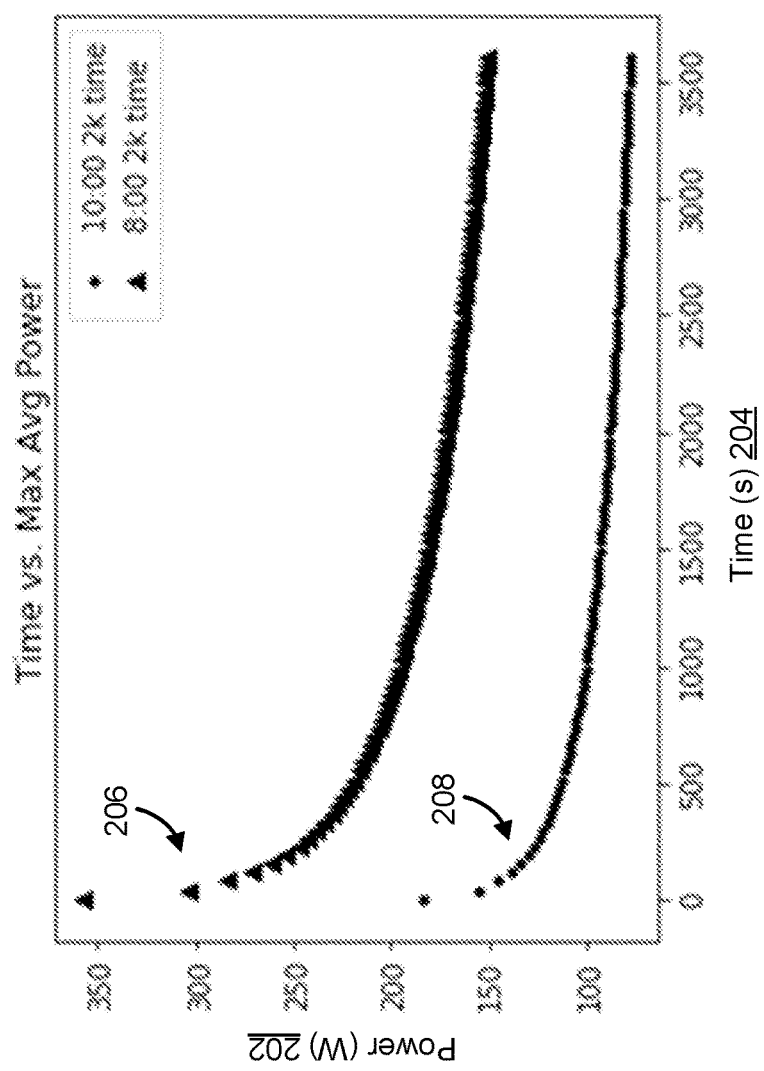
FIG. 2 illustrates an example power output curve during physical exercise for a user, in accordance with at least one embodiment.

FIG. 2 illustrates an example power output curve 200 for a user, which may represent part of a fitness profile for a user, such as may be generated by fitness profile generator 114 described above in reference to FIG. 1. Graph 200 represents the maximum average power the athlete could exert over a fixed period of time. As such, the y-axis 202 represents the maximum power in Watts, while the x-axis 204 represents the time in seconds. The athlete represented by the triangle-dotted line 206 rowed the 2 km test in 8 minutes, while the athlete represented by the circle-dotted line 208 rowed the 2 km test in 10 minutes. Their expected power decays very quickly as time increases from zero, but decays much more slowly over longer periods of time.

In some cases, the power curve of fitness profile 200 may be generated via the following techniques. In one example, a baseline measurement of performance on a modality-specific test is obtained. For one preferred embodiment of a rower cardio machine, this test can be a single 2,000 meter row. This distance of 2 km was specifically chosen because it represents a balance between power- and endurance-specific fitness adaptations. So, as a single test, it can enable determining an algorithm or function that predicts the user's performance at various times and distances.

For example, using the time it takes a user to row 2 km, an equation or function that encapsulates their expected performance at various other times and distances can be determined. This equation in one example looks like:

$$P(t) = A - B * \ln(t)$$

In the example equation above, P is power, A is a coefficient representing the theoretical maximal power at t=0, and B is a coefficient representing the decay of continuous power application over time. Through experimental modeling, rowing coaches have determined the maximum power a rower can exert over a ten-second interval (a baseline time for maximum power exertion) is 1.73 times the average power exerted over the 2 km distance. This maximum power may be used to generate the two coefficients A and B, which can be used for estimating power at various times and distances. These coefficients are multiples of the maximal power, determined experimentally.

For example, an athlete whose time to row 2 km is 8:00 (eight minutes, zero seconds) has exerted an average power of 202.5 W (given by $(2.8/(t/2000)^3)$) to accomplish that. The coefficients A and B, for that user, may be determined as follows:

$$A = 202.5 * 1.73 * 1.253; \quad B = 202.5 * 1.73 * 0.101$$

Thus, this example athlete's fitness profile can be represented in some embodiments by the equation: $P(t) = 439.07 - 35.55 * \ln(t)$. Through experimentation and data regressions, it has been determined that the best model to represent fitness decay over time in various examples is one of logarithmic decay. This decay can be due to fatigue—as the athlete fatigues over continuous effort, the maximum power they can exert over that time can decay logarithmically.

With this example fitness profile 200 created, in various embodiments, workouts can be dynamically adapted to fit the user's capabilities. Structured workouts can take the form of a series of intervals with varying prescribed time and intensity. Undulating intensity throughout a workout can be desirable in some examples to regulate fatigue while maximizing adaptations. The form this takes in cardio equipment on the market today is with verbal, subjective, often vague cues. "Medium intensity," "75% intensity," "maximum intensity" are examples of cues used by instructors to elicit the desired intensity by the athlete. However, these are vague, difficult to track, and difficult for the athlete to follow, which can be undesirable in many cases.

Instead, with a fitness profile in hand, some embodiments use the prescribed intensity of the interval, along with the overall workout's duration, to find a point along this curve. For example, for a one-minute interval with 75% intensity, in a thirty-minute workout, the point along this curve can be identified representing sixty seconds. The value at that point can then be multiplied by 0.75, then further reduced to account for sustained fatigue over a long workout, and a prescribed power to sustain may be determined.

An issue can arise in some examples from employing more precise intensities to dictate workout goals by representing these intensities. Athletes may need to be able to group relative intensities to form a mental model for what a specific intensity represents for them. In various examples it can be desirable for such a mental model to be intuitive, and/or readily apparent without thinking. That is—prescribing an athlete to be between 250 W and 300 W for a period of time may be more abstract than many athletes are capable of dealing with. Additionally, this prescription has no direct notion of relative intensity. While the prescription may have been derived from a maximal intensity, this may not be immediately apparent from seeing this number. Under fatigue, all of the problems with this sort of system can be exacerbated. This helps to explain why cardio fitness equipment tends to rely on vague prescriptions for relative intensity. These can be more readily understood by athletes under fatigue (though still can have issues with fidelity).

Instead, various embodiments include techniques, such as performed by a fitness profile generator 114, to show the user a representation of their entire intensity range by grouping it into four "zones". (Note that the example of four zones should not be construed to be limiting on the wide variety of alternative embodiments that are within the scope and spirit of the present disclosure, including any suitable plurality of zones, such as two, three, five, six, seven, eight, nine, ten, or the like).

Four zones in some examples can be used to simplify the thought process behind the prescription: if an athlete is told to get into the "sprint" zone, their mental model has some intuition about what that means. However, in various examples, precise intensities may be prescribed to dictate workout goals. Thus, some embodiments use the model described above to come up with four zones (or other suitable number of zones). For example, four points along the graph describing the user's performance capabilities may be selected and then adjusted for intensity thresholds to account for fatigue. So, an example "sprint zone" can be formed with the notion of >90% intensity. Because sprint intervals can be short in various examples, it may be reduced by a small amount. The next example interval down can be thought of as 70-90% intensity. But because these intervals may be longer (because the athlete may be able to sustain this intensity for longer periods of time), the power can be reduced by a greater multiple (e.g., by taking a point along the curve and dividing by a fixed factor). Doing this for all example intervals, power boundaries between each zone can be determined. In one example, these boundaries end up working out to:

Sprint: >88%
Race: >64%
Steady: >44%
Paddle: >26%

These boundaries are provided as merely an example and should not be construed to limit the wide variety of boundaries that are within the scope and spirit of the present disclosure in terms of the size and number of zones, and the like. While numerous examples of utilizing training zones are described in fitness training literature, the formulation of inherently intuitive zones, to aid a user in readily understanding effort, and the presentation thereof, using the techniques described herein is not present in known literature.

In various examples, these intensity levels can be represented as linear zones of speeds. Power can be an abstract metric—it can be difficult to explain what a certain wattage corresponds to in real-world outcomes. But speed can be an intuitive metric: it tells the athlete how far they go in a certain period of time. Linear representation is chosen in some examples to simplify the mental model for the user. Even though the zones themselves are not equal in size, representing them linearly in various examples can allow the user to understand their relative intensity with less effort than if their intensities were more precise. Further, in some embodiments, as the fitness profile is recalibrated and refined over time, the exact proportions of those zones may change. As such, the zones may be represented in various examples by setting even spacing between the speed boundaries. For example, when an athlete is rowing, their speed may be obtained and the corresponding zone determined. The speed can then be mapped or placed proportionally within the zone by taking the proportion of this speed to the speed difference between the top and bottom ranges of the zone.

FIGS. 3-5 illustrate example visual representations of intensity correlated with speed, such as may be provided by the fitness zones component 106 of user interface 104 of a fitness system 102 described above in reference to FIG. 1. FIG. 3 illustrates an example graphical user interface 300 that represents intensity in 4 zones, each corresponding to a range of speed or time to perform a certain task or fitness objective. Interface 300 corresponds to rowing, and thus separates intensity into zones labeled paddle 302, steady 304, race 306, and sprint 308, which correspond to different levels of effort (e.g., based on power output). It should be appreciated that different labels, different number of zones, different ranges of different zones, etc., may be utilized for different types of activity. In one example, cycling may be broken into different zones corresponding to normal or flat, hill climb, sprint, and recovery or downhill. Similarly, in another example, running may be broken up into different zones, such as warm up, slow, fast, and sprint. Each of these zones may be configured to correspond to varying intensity levels and ranges of intensity, similar to the rowing example described in more detail above.

In some aspects, the metrics that define one or more intensity zones may be represented in the time it takes to perform a certain activity, such as row a certain distance (e.g., 500 m). In some cases, speed, pace, vertical distance traveled, or other characteristic of the exercise activity may be used to define or represent different intensity zones. In some cases, various other metrics of the exercise activity may be displayed through graphical user interface 300, as illustrated, to enhance the user experience and/or communicate other useful and/or typical information usable by an athlete to improve training.

FIG. 4 illustrates another example user interface 400, where intensity zones are represented horizontally across the screen. For this example athlete, the interval in progress has prescribed Steady intensity (~44-64% relative intensity). This corresponds to speeds of 2:23/500 m to 2:10/500 m. (Rowing speeds are generally expressed as time to row 500 meters at that pace. These numbers correspond to 3.50 m/s and 3.85 m/s, respectively.) The athlete is currently rowing at 2:01/500 m (4.13 m/s), or above the intensity prescribed. In the method described below, in some examples, this may be considered as outside of the prescribed intensity. The success ratio for the user may not include this time. However, when considering performance against expected for recalibration, going above the expected intensity can be a signal the athlete's fitness has increased. This will be further described and expanded on in the examples discussed below. FIG. 5 illustrates another example interface 500, similar to example 400, but representing the zones vertically. Representing the zones vertically is another embodiment that can present training experiences that map to athletes' mental models of intensity in a different and potentially more intuitive way. It should be appreciated that interfaces 400 and 500 may also be configured to include a different number of zones, and/or different metrics to represent those zones.

Figure 6:
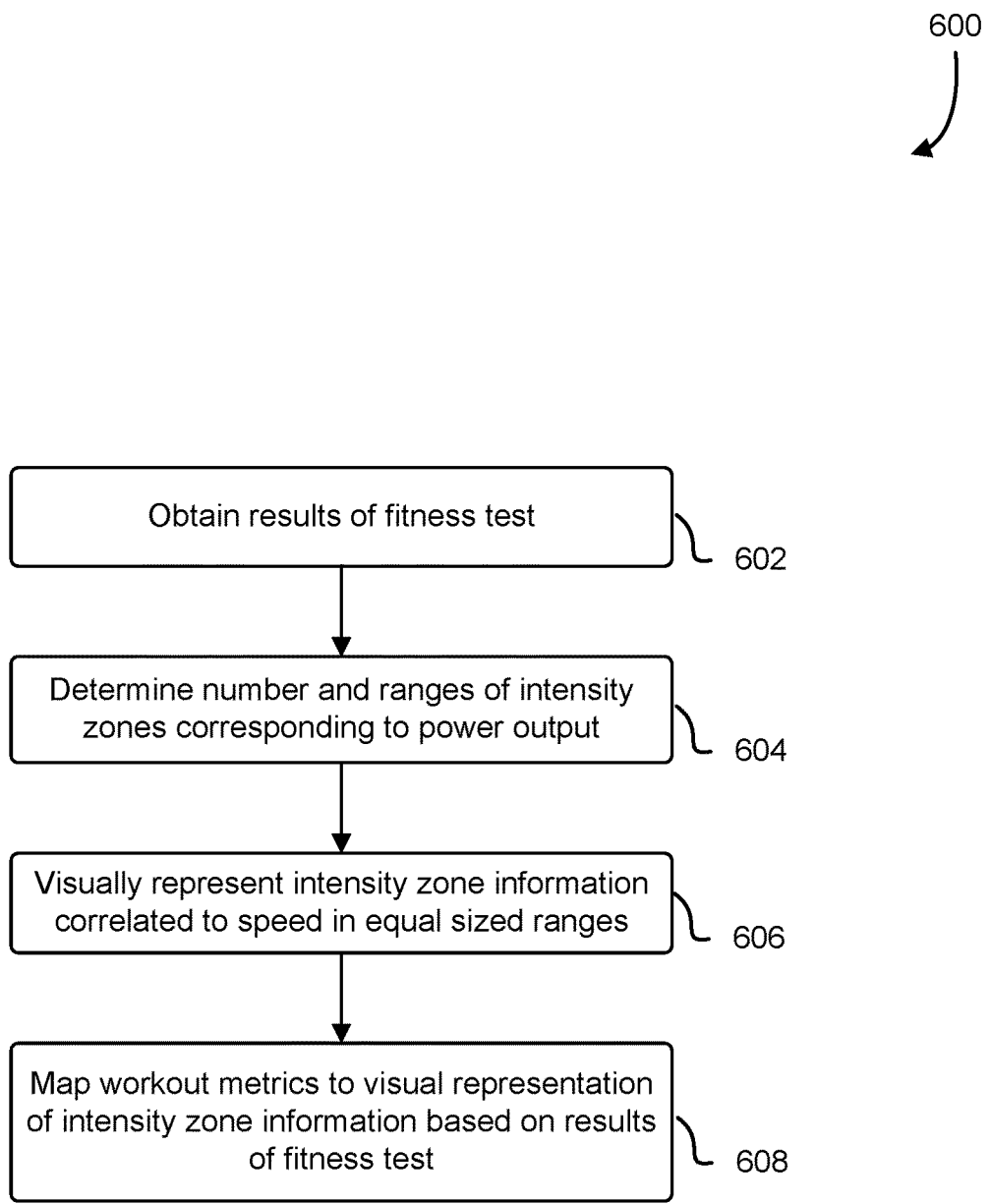
FIG. 6 illustrates an example process for visually representing intensity of a user's output within intensity zones, in accordance with at least one embodiment.

FIG. 6 illustrates an example process 600 for determining a fitness profile of a user and using that fitness profile to represent user output during a workout. In some aspects, process 600 may be performed by one or more of a fitness profile generator 114 and or user interface 104 of fitness system 102 described above in reference to FIG. 1.

As illustrated, process 600 may include first obtaining results of a fitness test, such as a 2 km row, from fitness equipment 124 or 130, at operation 602. Next, a number and corresponding ranges of intensity zones may be determined based on power output of the user during the fitness test, at operation 604. The intensity zone information may then be represented visually, such as via one or more user interfaces 300, 400, and/or 500 described above, at operation 606. In some cases, each intensity zone may be represented as being the same size, such as through using the same physical space in a user interface to represent each zone. In the rowing and other examples, the intensity may additionally or alternatively be translated to represent a physical characteristic of the workout, such as speed. At operation 608, workout or performance metrics from a user operating fitness equipment may be translated to the visual representation or user interface, to represent current metrics of the user's performance, at operation 608. In some cases, operation 608 may include representing a given intensity proportionally within a special area that represents the metric. In the example of speed, the user's actual speed may be mapped to a location within a box representing speed of a zone, where the location is determined speed on where the obtained speed falls within the zone.

Another method of various embodiments, then, is around measuring success of workouts. Current methods use aggregate mechanisms to measure the success of the workout: aggregate distance, average power, etc. These measures are imprecise, and don't take into consideration the nuances of structured workouts. With a structured workout, an athlete could, for instance, fail to reach a "sufficient" threshold in one interval but "make up for it" later on. If only looking at the average power, the system would miss that this occurred. If this were, for instance, a chronic miss by an athlete who had an unbalanced fitness profile, in which their sprint qualities were diminished, but their endurance qualities augmented, the system would never account for that, which may be undesirable.

Accordingly, various preferred embodiments include a method to measure success that allows us to account for individual differences in the athlete's sprint- and endurance-fitness qualities. By measuring ratios of time spent in these specific intensity zones, compared to the prescribed intensities, in various examples, numerical representations of the athlete's performance can be derived for that workout. For example, the ratio of time spent in each prescribed intensity zone to the time prescribed for that intensity zone can be determined. This series of ratios can then be aggregated to provide an overall ratio for the workout. In this manner, various nuances in an athlete's fitness may be readily determined, such as an athlete with an unbalanced fitness profile who tends to miss sprint-focused intervals, while succeeding on long, endurance-oriented intervals.

This multi-variate success metric can be particularly useful when applied to adapt a fitness profile for a user to thus adapt fitness workouts for that user. To that end, various preferred embodiments include a method to adjust the athlete's fitness profile over time. Cardio equipment historically has not adjusted the fitness profile for an athlete. Or these machines require the user to manually make adjustments or input a univariate assessment. Accordingly, some preferred embodiments include a method to recalibrate an athlete by using historical workout results.

Over the course of a workout program, an athlete can develop adaptations that improve their performance. However, these adaptations may not be uniform across various qualities. So, for instance, an athlete genetically predisposed to strong performance in endurance activities may improve their endurance fitness more than they improve their sprint fitness, when dedicating a similar amount of training time and/or effort to both types of fitness.

Because various examples can track athlete performance and success at the individual intensity level, not just at the aggregate workout level, it is possible to determine how the athlete has performed over time in various contexts. Some embodiments then can recalibrate the user, as described in greater detail below. Through the initial calibration, an estimate of the athlete's performance in each segment of the workout can be calculated. In various embodiments, this estimate can take into account one or more of: the prescribed intensity level of the interval, the intensity levels of the preceding and subsequent intervals (to account for accumulated and expected fatigue, respectively), and post hoc assessment of perceived exertion to calculate one or both of:

Expected ratio of time in prescribed intensity zone

Expected average power and aggregate distance

Using this success criteria on an interval-by-interval basis can allow determining if the athlete is meeting expectations, falling short of expectations, or exceeding expectations. Additionally, the relative intensities of the intervals can allow isolating changes to specific aspects of a user's fitness. Using a post hoc measure of perceived exertion in some examples can further help refine this assessment.

Periodization theory dictates that for fitness growth, training can be broken up into discrete cycles. After each cycle, a test can be used to assess performance. Some preferred embodiments of a recalibration method draw inspiration from this idea and apply it to cardio equipment. An athlete's periodization plan is typically custom-built by a coach manually overseeing their progress. In some aspects, because the described techniques measure success and expectations in this granular fashion, it is possible to apply a periodized model automatically. By collecting results over a fixed-length cycle of a suitable number of workouts for the modality and athlete, the athlete's performance can be assessed against their expected performance and a growth score may be determined and assigned to that athlete.

Figure 7:
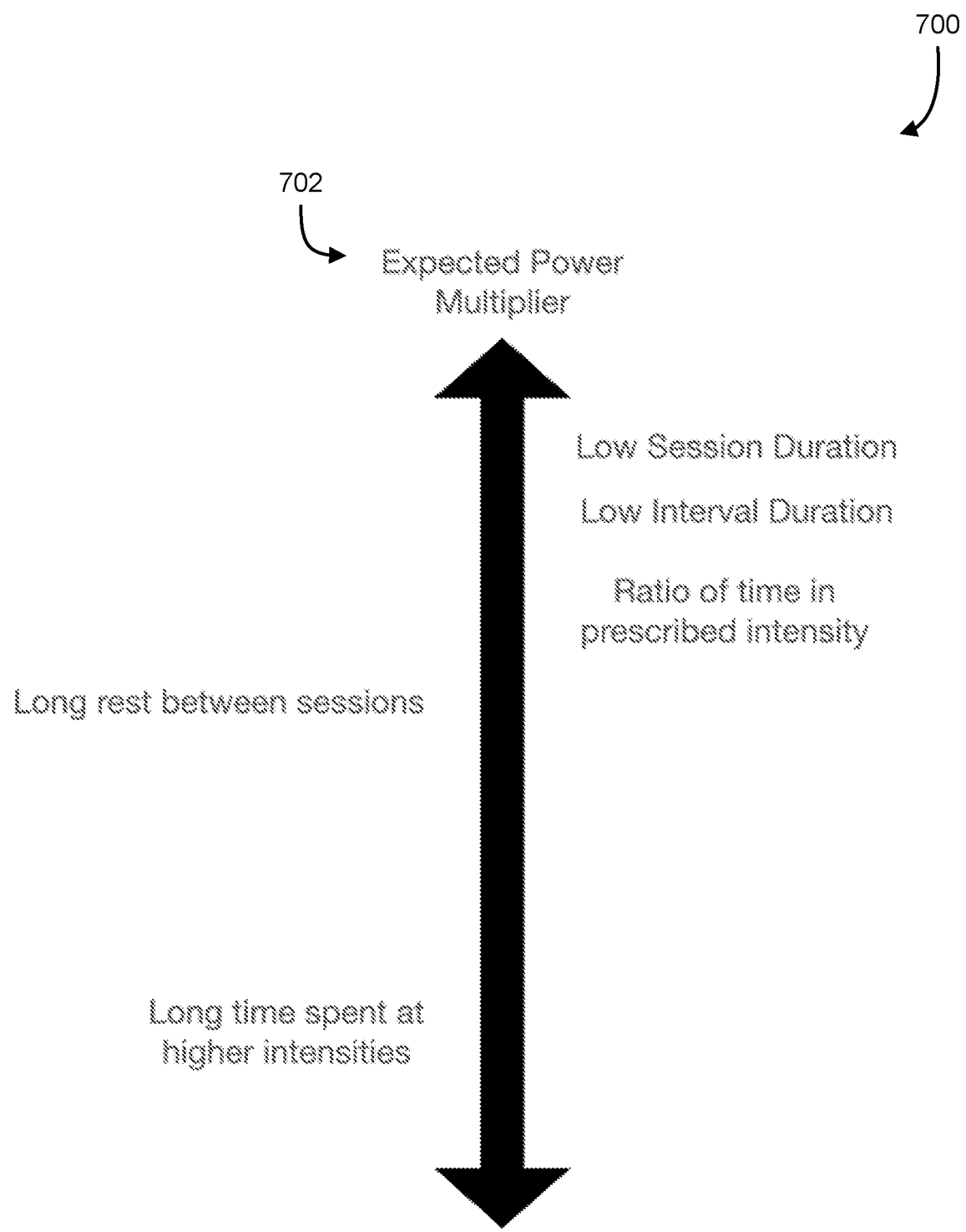

In some aspects, an athlete's power output may be calibrated on a micro and/or macro level. As discussed above, preceding and subsequent intervals in a single workout can affect an athlete's output in a particular interval. Similarly, characteristics of different workouts or fitness sessions and the time in between those sessions, may also be factored into developing and modifying a fitness plan for an athlete. Different representations of the relationship between intensity and time, as it may affect an athlete's output, is illustrated in FIGS. 7 and 8. As illustrated by diagram 700 of FIG. 7, the expected power multiplier 702 for any given time/workout is affected by characteristics of prior workouts or fitness sessions, including intensities and durations of those workouts, and time in between those workouts. In some cases, duration of different intensities levels in one or more prior workouts may also affect tan expected or generated power multiplier, to be used to modify an athlete's fitness profile, as described in greater detail above.

Diagram 800 of FIG. 8 illustrates a different representation of various factors that affect changes in the expected power multiplier of an athlete. As illustrated, as rest between workout or fitness sessions increases, so does the expected power multiplier. Similarly, as average heart rate increases, so does doe expected power multiple. Session duration, interval duration, and ratio of time spent at higher intensities may adversely affect the expected power multiplier, such that an increase in one or more of these factors may lead to a decrease in the expected power multiple. In some examples, these various factors may be used to determine how much performance in past training sessions by an athlete may impact their expected performance.

FIG. 9 illustrates an example user interface (UI) 900 that represents a recalibration of a user's fitness profile in terms of their performance compared to their expected performance. In some cases, recalibration of a user or athlete's fitness profile may take the form of determining changes to their respective power output function, as described above.

As illustrated in UI 900, a user's current performance for a given intensity interval may be illustrated by pace 2:44 for a paddle intensity 902, pace 2:18 for a steady intensity 904, and a pace 2:01 for a race intensity 906. These performance metrics for these given intensity levels may be compared to an expected or prescribed performance for that intensity level, to adjust a user's fitness plan going forward. In some cases, adjusting the user's fitness plan may include changing a prescribed pace for one or more intensity levels, changing one or more time interval spent in a given intensity level, number of intervals in a given intensity level, etc., for one or more future workout plans or fitness sessions.

In the example illustrated, a user's prescribed or predicted performance may include a 3:00 minute pace for paddle intensity 902, a 2:25 pace for steady intensity 904, and a 2:05 pace for a race intensity 906. In this example, the user exceeded all of the prescribed performance metrics (in this case, speed to row 500 meters), and thus adjustments may be made to future workout plans to account for this increase in performance. In some cases, the adjustment may include adjusting the new pace metrics for each intensity level to the actual performance achieved in the current workout, or may include a more incremental adjustment, based on a number of factors, as discussed above.

Figure 10:
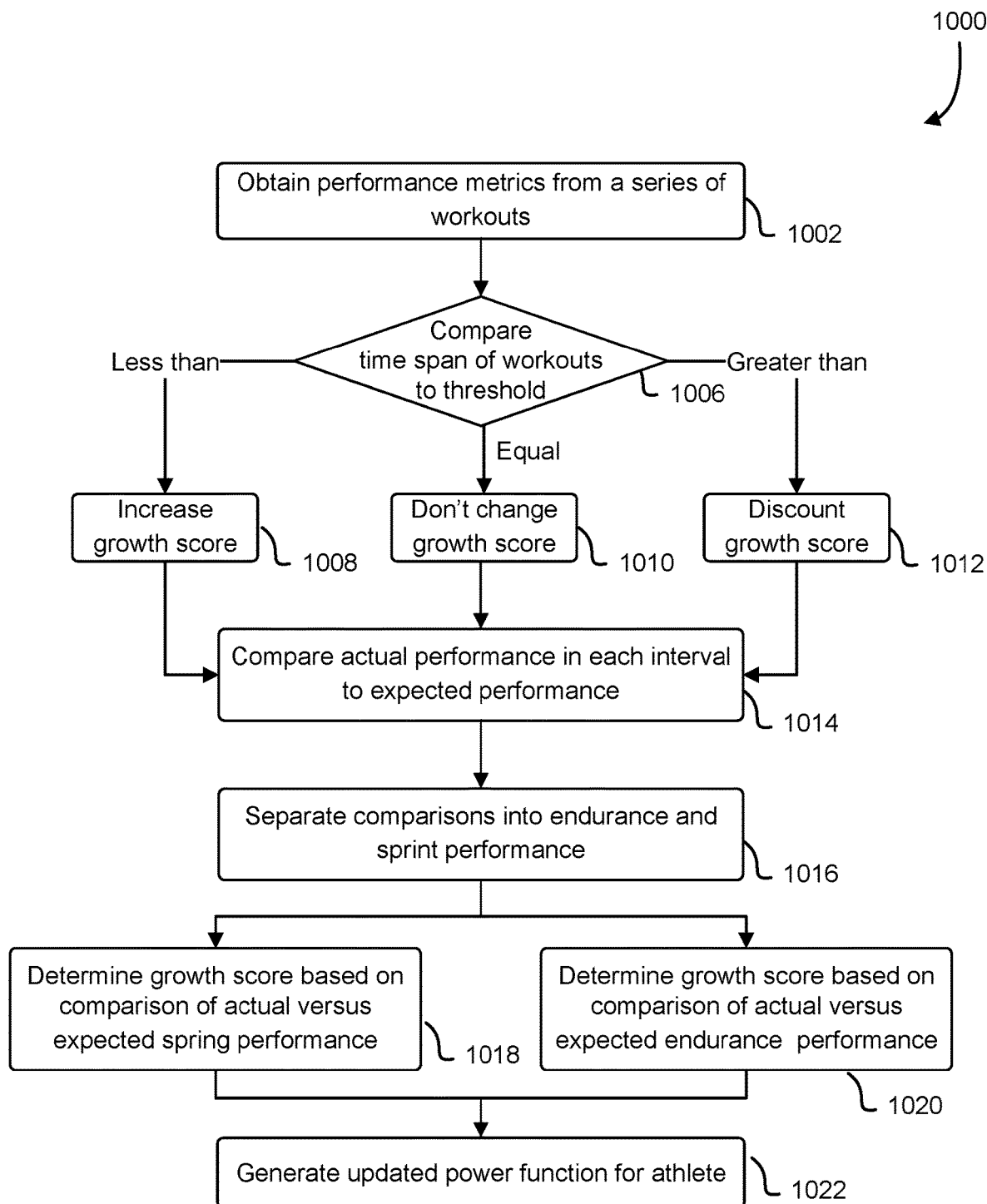
FIG. 10 illustrates an example process for recalibrating a user's fitness profile or power output function, in accordance with at least one embodiment.

FIG. 10 illustrates an example process 1000 for determining a growth score, or change in a user's fitness profile. In some aspects, process 1000 may be performed by one or more of a fitness profile generator 114, a fitness calibrator 116, and or user interface 104 of fitness system 102 described above in reference to FIG. 1.

In some aspects, a growth score may take the form of one or more mathematical changes to their power output function. In some aspects, a user's fitness profile or output function may be changed or recalibrated upon completion of one or more workouts or fitness sessions. In some cases, it may be advantageous to maintain a workout plan, which may include a number of workouts, with little modification until a longer period can be observed, to then inform more accurate changes to the workout plan/individual portions of workouts of a workout plan. The length of a time period observed may vary. In some cases, 30 days may represent a suitable period to observe as in that time, the human body has time to adapt to training stimulus and change. It should be appreciated that the described systems and processes are easily adaptable to accommodate different users, different time periods, different types and end goals of training, and the like.

In the example illustrated, process 1000 may begin by obtaining performance metrics of a series of workouts for an athlete, at operation 1002. An example set of performance metrics or data for a series of workouts will be discussed in greater detail below in reference to FIG. 11. In some cases, the performance data obtained may include any of the performance data discussed above, such as in reference to FIG. 1. The time period or span of the series of workouts may be examined and compared to one or more thresholds, at operation 1006. In one example, a time period of 30 days may be used as it is considered standard (although other suitable standard time periods can be used): if the time period is determined to be greater, at operation 1012, the score may be discounted slightly. If the time period is smaller, as determined at operation 1008, then more credit or growth may be assigned to the user, as the user will have accumulated more fatigue, so their performance is less representative of their peak performance. In the event the time span is equal to the threshold, such as 30 days in this example described, then no global changes may be made to the growth score, at operation 1010.

Next, at operation 1014, actual performance in each workout interval may be compared to the expected performance of that respective interval. In some cases, operation 1014 may include comparing each interval in each workout, where each interval may span any of a variety of lengths of time (e.g., ranging from 10 or 15 seconds, up to 1, 2, 3, 4, 5, 10, 15 minutes etc.). In other cases, different intervals (e.g., a subset of the total number of intervals in a given workout) may be selected for comparison based on a number of factors, such as to reduce the amount of computation necessary to calculate the growth score. In these scenarios, intervals may be selected through each workout (e.g., evenly spaced throughout the workout), where the same intervals may be selected for each workout to then provide an accurate comparison of performance across a number of similar workouts. In other cases, such as when the workouts are different, different criteria may be utilized to select some or all of the intervals in the individual workouts to provide an accurate representation of training progress. In some cases, intervals at the same relative time within the work may be selected for comparison. In yet some cases, the intervals with the highest intensity of a given workout may be compared. In yet some examples, different observations and conclusions may be derived from examining intervals that are different between different workouts, such as, for example, to determine or differentiate sprint fitness versus endurance fitness. The differences observed in this example may be used to more heavily weight one of sprint or endurance training in a subsequent workout.

At operation 1016, one or more intervals of the observed workout or workouts may be separated into intervals representing sprint (e.g., shorter time periods, high power output, higher speed, etc.) and endurance (e.g., longer time periods, slower speed, more sustainable power output) performance. In some cases, operation 1016 may include separating out individual time intervals of a given workout, or groups of time intervals in a workout. In other cases, operation 1016 may include separating out entire workouts.

In either case, the athlete's performance in each of these different categories of fitness performance for a time period (e.g., interval, group of intervals, or entire workout) may then be compared to determine a sprint performance growth score, at operation 1018, and an endurance performance growth score, at operation 1020. In some cases, operations 1018 and 1020 may include determining the ratio of expected performance in each category to the actual performance. The determined ratio can then inform how to adjust each component of a fitness model to meet the user's new performance characteristics. These growth scores can take into account accumulated fatigue and individual differences, and as output, can emit a new logarithmic model representing an estimate for the user's current fitness, such as inputs to generating an updated power function for the athlete, at operation 1022. An example determination of a growth score/changes to an athlete's power function will be described below.

In some alternative embodiments, operation 1016 may include separating one or more intervals of the observed workout or workouts into any number of different categories based on a variety of metrics, such as known fitness metrics. In some cases, intervals may be separated into different categories or groups based on body mechanics and/or energy systems, such as into intervals falling into exercise categorized as one of aerobic, anaerobic-alactic, and anaerobic-lactic. In this example, different intervals may be categorized into one of these different categories based, at least in part, on heart rate obtained from a user, which may be further modified based on energy systems or detected attributes of individual users. In some examples, these or other interval categories may be defined or refined based on how a user responds to different training stimuli, including changes in heart rate, and other biometrics. In the multi-interval category, a growth score may be determined for each different interval category or classification, as alternative operations to operations 1018, 1020. The different growth scores may then be combined to determine one or more updates to a power function of the user, as an alternative to operation 2022.

In one illustrative example, an athlete may perform a single workout ten times. FIG. 11 illustrates a table 1100 showing results for 10 sample workouts. In this example, the second line in the first row represents the expected results for the interval. These expected results are the same for all ten rows, so they are only listed once. Each row represents the distance rowed in that interval, along with the ratio of time spent in the prescribed intensity zone. In various embodiments, the system can account for one or more of the following:

The workout on 1/11 is an outlier: occasionally athletes will show fatigue that is due to factors outside of their general fitness, which can be detected Interval 1's expectation is consistently beaten Interval 2's expectation is consistently missed Interval 1 on 1/8 had an underperformed ratio, but an overperformed distance. This may still be assessed as overperforming, given the context of Interval 2 (the athlete outperforming their own average)

As such, in various examples, the described system and techniques can assign a growth score to account for knowing that short intervals (e.g., representing sprint performance) should be calibrated higher, while long intervals (e.g., representing endurance performance) should be calibrated lower. In one example, a sprint growth score of 1.09 and an endurance growth score of 0.85 may be determined and assigned. A new model can be generated automatically by applying these as ratios to the user's power input used to generate the coefficients. The new user profile or power output equation in this example then becomes:

$$P(t)=479.03-30.0*ln(t)$$

As this model can represent the athlete's new fitness profile, it can be used for subsequent workouts in the following cycle. The athlete can see the speed necessary to achieve higher intensity zones raised. However, they can also see speed necessary to achieve lower intensity zones reduced. So, the example workout above can have an expected distance of 125 m, followed by an expected distance of 1,750 m. In this way, users who progress can see their adaptations reflected in workouts with higher absolute intensities, even as relative intensities remain steady. Higher absolute intensities in prescriptions can push athletes to improve and can create a feedback cycle by which they are constantly encouraged to improve to see results. Athletes who lose fitness (such as after recovering from an injury or other long layoff) can find their fitness profile adjusted downward automatically to compensate and can be encouraged to train to bring it back upward.

Figure 12:
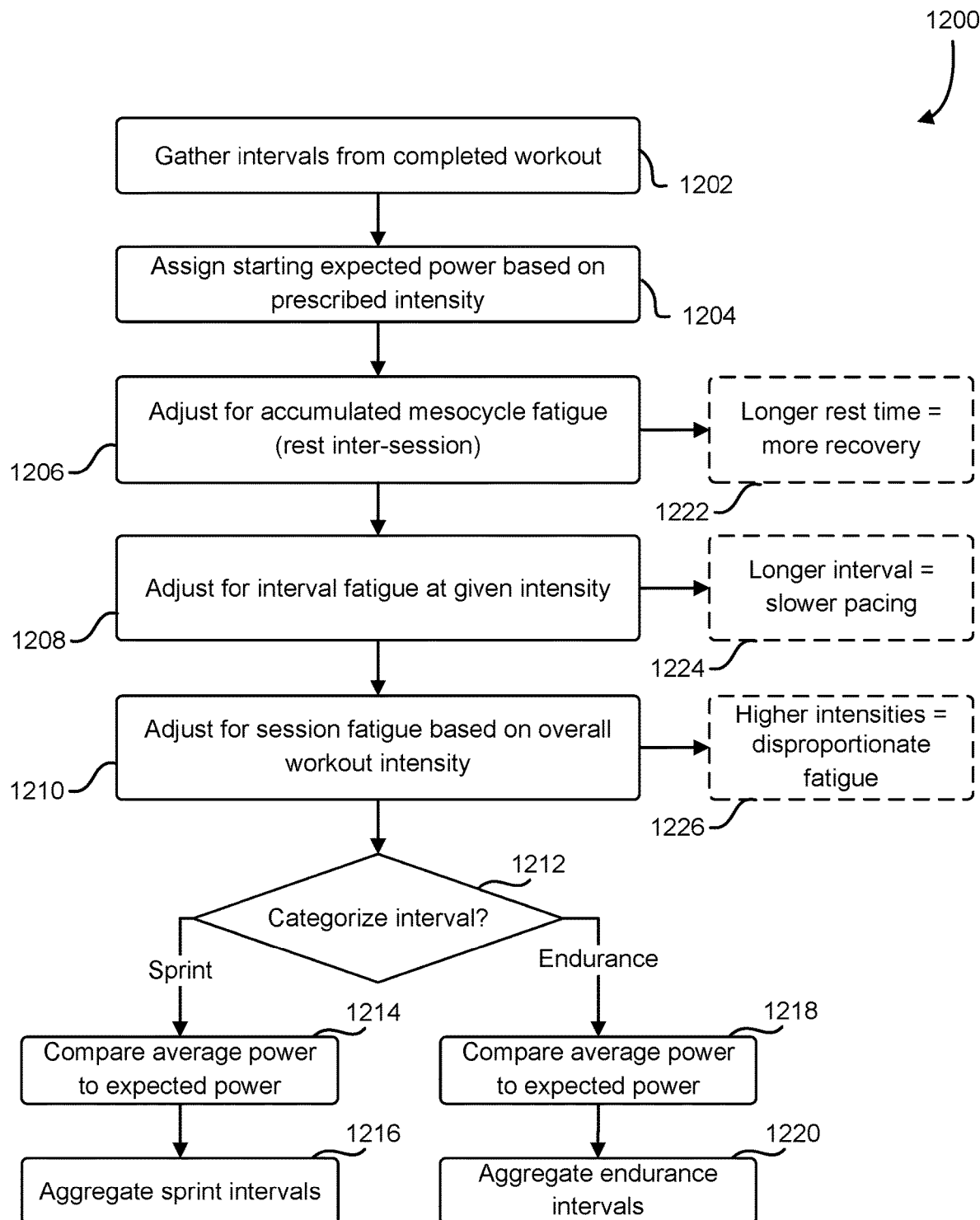
FIG. 12 illustrates another example process for recalibrating a fitness or workout plan, in accordance with at least one embodiment.

FIG. 12 illustrates another example process 1200 for calibrating a fitness or workout plan. In some cases, process 1200 may be employed to adjust a given workout based on prior activity of the user, such as including a past completed workout. In some aspects, process 1200 may be performed by one or more of a fitness profile generator 114, a fitness calibrator 116, and or user interface 104 of fitness system 102 described above in reference to FIG. 1.

Process 1200 may begin at operation 1202, in which information pertaining to intervals of a completed workout may be obtained. In some cases, this information may include the length and number of intervals, the prescribed intensity level of the interval, the actual performance of the user during the interval, and/or a date and time of the past workout. Next, a starting expected power may be assigned to a current or future workout interval based on the prescribed intensity of the workout, such as included in the workout/fitness plan, at operation 1204. Next, the expected power output of the user for the interval/workout may be adjusted for accumulated mesocycle fatigue, such as based on inter-session rest, at operation 1206. In some cases, a longer rest time in between workouts may correspond to greater recovery, meaning the output power can be adjusted to be higher, and vice versa, at 1222.

At operation 1208, the expected power output of the user for the interval/workout may be adjusted based on interval fatigue at a given intensity. In some cases, a longer time interval of the workout may correspond to slower pacing, and vice versa, at 1224. Similarly, the expected power output of the user for the interval/workout may be adjusted for session fatigue based on overall workout intensity, at operation 1210. In some cases, higher intensities may correspond to disproportionately higher fatigue, such that the relationship between higher intensities and fatigue is not linear, but rather approaches exponential, as indicated at 1226.

Next, each interval of a workout may be categorized as either a sprint interval or endurance interval, at operation 1212. In both cases, the average power of the respective category of interval may be compared to the expected power of that interval, at operation 1214, 1218. The sprint interval results may then be aggregated, at operation 1216, and similarly, the endurance intervals may be aggregated, at operation 1220 to produce some type of sprint score and an endurance score. In some cases, this information may then be used to change the output power function of a given user, as described in more detail above, to recalibrate the user's fitness plan going forward.

As described above in reference to FIG. 10, in some cases, intervals of a workout or spanning multiple workouts may be divided based on criteria other than whether an given interval falls into one or sprint or endurance performance, such as based on whether an interval falls into one of an aerobic interval, an anaerobic-alactic interval, and an anaerobic-lactic interval. In this example, the average power in these different intervals may be individually compared and results for those different interval types may be aggregated, as alternatives to operations 1212, 1214, 1216, 1218, and 1220. It should be appreciated that other categories of intervals may also be similarly implemented to produce similar benefits.

Further embodiments include a set of methods for dealing with races. The above description of calibration, workout adaptations, and recalibration can be applicable for structured workouts (training). However, an important mechanism for training in some examples is competition. Many athletes approach training with the end goal of participating in some sort of competition to test their skills. However, most competition requires users to be competing at the same time. This presents challenges with those who wish to compete at odd hours—for instance, those with young children whose training and competition hours are limited to after the kids are asleep. Further, it can limit competition to those who are in similar time zones. If the two best athletes on a platform are in vastly different time zones, the inability for them to compete can be detrimental to both.

To address this problem, various preferred embodiments include a method to allow asynchronous races to be recorded, and then simulated in a synchronous fashion. For example, while an athlete is competing in a race, fitness system, such as the fitness system 102 and/or a race simulator 118 described above in reference to FIG. 1, periodically capture various users of exercise equipment 124, 130 and their corresponding performance data to simulate their progress in a workout, which may take the form of a race. In some cases, the performance data may include one or more of: the elapsed time, the distance traveled, the instantaneous speed, and the stroke state. An example of the performance data obtained is provided below:

Sample: {elapsed: 2000 ms, distance: 1000 mm, speed: 500 mm/s, stroke state: drive}

Various sorts of athletic motion can be continuous: there can be a continuous state with respect to time. But it may be desirable to capture this information in discrete chunks and store it in an easily accessible place, such as a central database (e.g., data store 120 of system 100). Thus, it can be desirable to come up with a sample rate that allows capturing all information necessary. A suitable sample rate to capture any particular endeavor can be dependent on the specifics of the endeavor. For rowing, the modality tested for some embodiments, a race simulator or other mechanism can capture enough information to determine one or more of: when a stroke starts; the power generated in that stroke; the speeds necessary to recreate the motion from that stroke; and the like. To come up with an effective sample rate, in some examples, bounds of these requirements may be determined. In one example, power generated in a given stroke may be easy to obtain and then map to performance for race simulation. In order to capture this information, the selected sample rate should be able to distinguish a stroke start. Rowing stroke frequency can be expressed in strokes per minute (SPM). Typical rowing SPMs fall in the 18-34 range. The power portion of a rowing stroke typically lasts about ⅓ of the total stroke-recovery-catch cycle. Thus, if a sample stroke rate of 34 (not a strict upper bound, but a reasonable example to use) is selected, the power portion of the stroke in this example spans a time duration of:

60000 (ms/min)/34 (strokes/min)=1764.7 (ms/stroke)
*⅓=588 ms

According to the above example, the power portion of the stroke can take >=588 ms. So, a sample period of 500 ms (rate of 2 samples/sec) will allow detecting the power portion of the stroke in this example. But, that sample rate does not enable effectively detecting the power generated in the stroke, in this example. To capture power generated in a stroke, a high sample rate is needed. Otherwise, information of the stroke at the end may be captured, which would cause loss of information about the specific power generated at the start of the stroke. Accordingly, a higher sample period, such as 100 ms (rate of 10 samples/sec), may be selected. It should be appreciated that other sampling rates/periods are contemplated herein and may be utilized advantageously to a similar effect.

Figure 13:
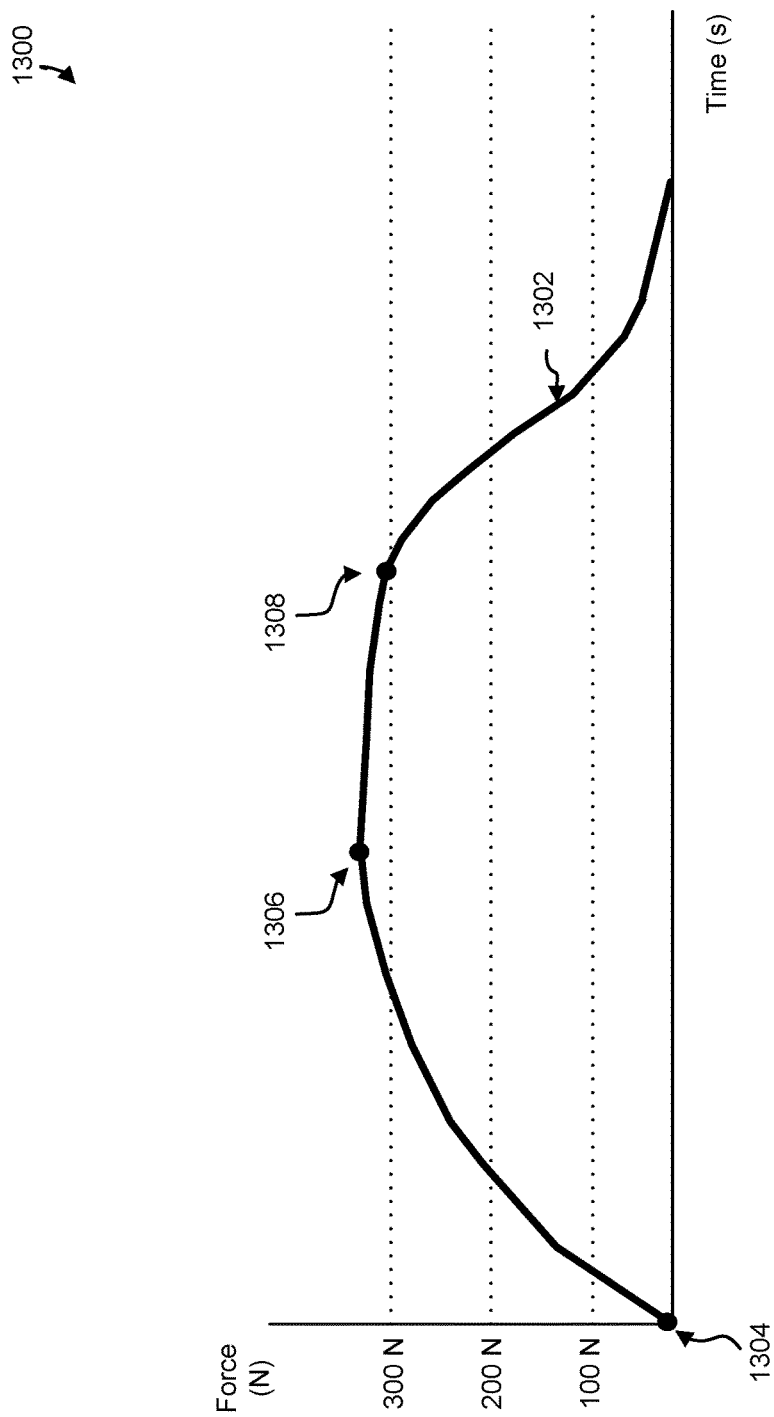
FIG. 13 illustrates example force curve generated during a stroke while rowing, in accordance with at least one embodiment.

FIG. 13 illustrates an example 1300 of a typical force curve 1302 for rowing over a period of time. The upward motion, represented by force curve 1302 between points 1304 and 1306 is known as the drive: when the athlete applies force with the legs, trunk, and arms to propel the boat forward (or in the case of indoor rowing, the flywheel mechanism providing resistance). The peak of the drive, at point 1306, is at the midpoint of the drive, when the legs, trunk, and arms are all at their maximal mechanical advantage. Point 1308 on the curve 1302 represents that end of the application of more force, where the force curve dramatically drops off. A sample rate of 10/sec allows recreation of this force curve. By storing the instantaneous speed and stroke state, it is possible to reliably capture enough points to detect each of points 1304, 1306, 1308 in this example.

In various examples, performance data, such as captured at a determined sampling rate as described above, may be captured from a number of different users operating exercise equipment, such as exercise equipment 124, 130, and stored for simulating a race in one or more data stores 120 by a fitness system 102. In some aspects, performance data may be captured by individual pieces of exercise equipment and at some time communicated to a centralized data store, such as data store 120. In one example, a first user may perform a race, which may be a certain class of fitness workouts, as described above. When another user performs the same race or workout session at a future time, all of the data captured relating to the first user's performance may be communicated to the second user's fitness equipment, to simulate a race. In some cases, the race simulator 118, described above in reference to FIG. 1, may direct or coordinate obtaining data between exercise equipment 124, 130 to provide for a race simulation in the individual exercise equipment.

Figure 14:
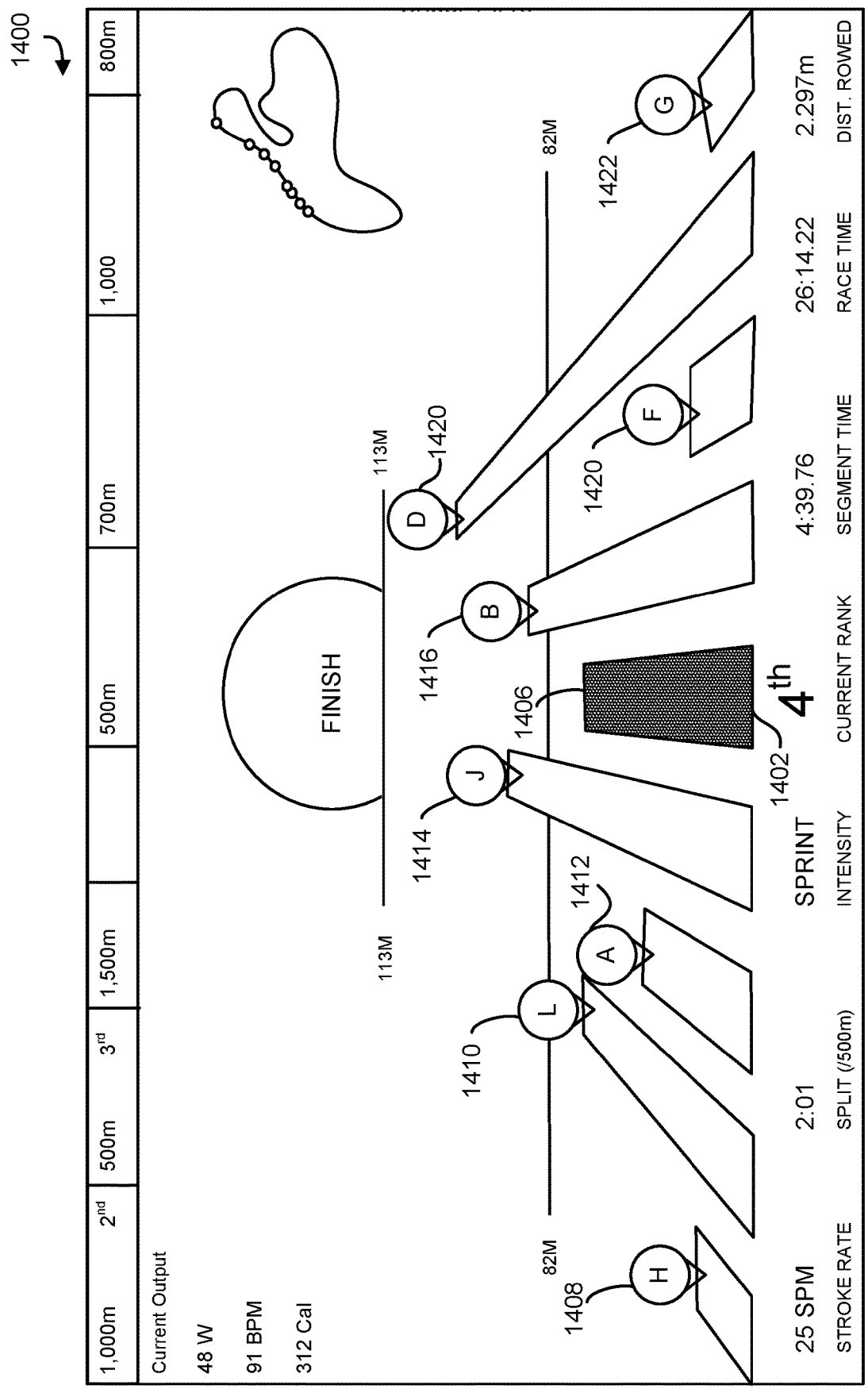
FIG. 14 illustrates example graphical user interface representing a simulated race, in accordance with at least one embodiment.

In some aspects, one or more user interfaces, such as graphical user interface 1400 illustrated in FIG. 14, may be generated to simulate a race scenario. In some aspects, the graphical user interface 1400 may be generated by a race simulation 110 of a user interface 100 of fitness system 102.

In the example user interface 1400, a current user's progress in the race workout may be represented by a bar or box 1402 in the center of a race screen. The position 1406 of the end of bar 1402 may be determined based on the operation of a piece of exercise equipment currently being operated by a user, such as a rowing machine. The progress of other racers, 1408, 1410, 1412, 1414, 1416, 1418, 1420, and 1422 may be determined and represented in screen 1400 based on previously captured performance data from performance of the same race by other users (or even the current user). In some examples, the information used to determine a current position of the other racers may be obtained from stored performance data corresponding to a different performance of the same race workout. In some examples, this performance data may be communicated to the current user's local exercise equipment or computing device, whereby the exercise equipment and/or computing device may generate the user interface 1400. In other cases, the user interface 1400 may be at least in part generated by a centralized or distributed system and communicated to the current user's exercise equipment.

In some aspects, one or more other indicators of progress, fitness performance, etc., may be provided in user interface 1400, as illustrated in FIG. 14, such as a representation of a race course showing relative positions of the users, other biometrics, summations of different information corresponding to a user's performance in different stages of the race, etc. In yet some examples, screen or user interface 1400 may represent the user's progress in 3 dimensions, such as interfaces similar to 1400, but representing a user's progress as a 3D shape, such as an arc having depth, points along a circle of sphere, etc.

When the race is being performed by the current user, the positions of the other racers can be interpolated from the sample performance data. In some examples a user position may be interpolated from sample performance data as follows. First, each stroke can be isolated from the performance data. Because the stroke state for each data point is stored, isolating or separating out each stroke from the data may include grouping each set of data points by starting with the "drive" stroke state, or a higher force value. Subsequent data points may then be examined to identify data that corresponds to data points 136 and 1308 described above in reference to FIG. 13. The remainder of the power curve, such as the example illustrated in FIG. 13, can be determined by fitting a logarithmic growth between points 1304 and 1306, and a logarithmic decay between points 1306 and 1308, and an exponential decay between 1308 and the start of the following stroke. Using this example process, a position of an athlete in a simulated race may be determined, tracked, and more accurately represented. The precision enabled by the above described techniques may be particularly desirable in a race setting, where difference between first and second place can be as small as 10 milliseconds. The described techniques may enhance the simulated race experience by accurately converting a set of discrete data points to a continuous distribution representing athletic performance, and accurately presenting that information to an athlete.

In some cases, user interface 1400 may be used to represent a multi-segment race. Just as it can be desirable to detect athletes who have different sprint- and endurance-fitness characteristics, it can be desirable to provide races allowing for athletes with different capabilities to express them. By subdividing a race into discrete segments, such as indicated by one or more distance or other markers, 1424, athletes can rank independently in segments of various distances. This can have the benefit of providing increased incentive for a sprint-focused athlete to compete in longer races: if they are able to express their fitness more fully in shorter segments, they may be able to get the benefits of a longer workout, while still claiming victory in a segment of a longer race. This can also allow using individual segment results to recalibrate a user, which can further reinforce the calibration ability and can allow for matchmaking based on expected results.

In some aspects, one or more of other racers, 1408, 1410, 1412, 1414, 1416, 1418, 1420, and 1422 may be users also performing the race training live or in time with a current user. In this example, both the current user and the live user's race performance may be sampled stored and communicated to the other racer at the determined sample rate, in order to capture the speed/progress of each user with a high degree of accuracy to improve the experience of the race for both live users.

In other examples, other activities besides rowing may be captured and used to simulate a synchronous race. In one example, running on a treadmill or even running outside may be captured and simulated in a race scenario. In the running example, the sample rate may be determined to capture granular changes in pace, particularly when undulating terrain is simulated, to better capture a user's speed, changes in speed, and progress through a race workout or course. In a similar way, bicycling performance of various users on a simulated track or course may be captured and used to simulate race. In this example, the sampling rate may be determined based on an estimated maximum revolution per minute for a given bicycle, which, in some examples, may be dictated by wheel diameter and/or gear selection.

FIG. 15 illustrates an example process 1500 for providing a simulated race experience. In some aspects, process 1400 may be performed by one or more of a race simulator 118, and or user interface 104 of fitness system 102 described above in reference to FIG. 1.

Process 1500 may begin at operation 1502, in which a sampling rate may be determined for a particular activity or exercise. In the primary example described above, this may include determining a sampling rate for rowing. However, it should be appreciated that a sampling rate for other exercises or activities may similarly be determined, based on movement characteristics of the particular activity. As with the rowing example, this may include determining the extremes of a range of the particular movement (e.g., a stroke in rowing, a revolution in cycling, a stride in running, elliptical, or Nordic skiing, a step in a stair stepping machine, etc.), and determining a minimum time period or sampling period needed to capture that range of movement. In some cases, one or more number of intervals or a duration of one or more intervals may be used to inform selection of the sampling rate. In some aspects, it may be more efficient to set a sampling rate based on all of the intervals in a race workout/course. In other examples, it may be advantageous to utilize different sampling rates for different intervals of a workout, such as having a higher sampling rate for sprint or faster intervals, or intervals of shorter duration, of a simulated race course and/or a slower sampling rate for longer or slower intervals, and the like.

Next, at operation 1504, fitness performance data for a given workout plan, course, etc., may be obtained when it is performed by one or a number of users, at the determined sampling rate. In some aspects, the fitness performance data may be stored in one or more user fitness data records or track or race records, such as a user fitness data record or partition 122, maintained by a data storage system 120. The fitness performance data may include any speed, power, acceleration, and other characteristics of performing the given exercise during performance of the race workout/course. In some cases, the fitness performance data may include one or more aspects of the fitness or performance data described above.

During or before performance of the race workout or course, by a current user, the obtained fitness performance data may be obtained, at operation 1506, and used to interpolate or generate data representing continuous motion or progress in the race workout/course, at operation 1508. Operation 1508 may include the process described above for using logarithmic growth and decay to represent various portions of a movement used to perform the activity. In other cases, various other functions may be used to approximate certain movement patterns (or other physical characteristics) in various activities.

The modified or interpolated fitness performance data of one or more other users may be presented, in time or synchronized with a current user performing the race workout/course, at operation 1510. In some cases, operation 1510 may include providing a user interface, such as the graphical user interface 1400 described above in reference to FIG. 14, to the user, to simulate an actual race scenario.

The described embodiments are susceptible to various modifications and alternative forms, and specific examples thereof have been shown by way of example in the drawings and are herein described in detail. It should be understood, however, that the described embodiments are not to be limited to the particular forms or methods disclosed, but to the contrary, the present disclosure is to cover all modifications, equivalents, and alternatives.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed but, on the contrary, the intention is to cover all modifications, alternative constructions, and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. Similarly, use of the term "or" is to be construed to mean "and/or" unless contradicted explicitly or by context. The terms "comprising," "having," "including," and "containing" are to be construed as open-ended terms (i.e., meaning "including, but not limited to,") unless otherwise noted. The term "connected," when unmodified and referring to physical connections, is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal. The use of the phrase "based on," unless otherwise explicitly stated or clear from context, means "based at least in part on" and is not limited to "based solely on."

Conjunctive language, such as phrases of the form "at least one of A, B, and C," or "at least one of A, B and C," (i.e., the same phrase with or without the Oxford comma) unless specifically stated otherwise or otherwise clearly contradicted by context, is otherwise understood within the context as used in general to present that an item, term, etc., may be either A or B or C, any nonempty subset of the set of A and B and C, or any set not contradicted by context or otherwise excluded that contains at least one A, at least one B, or at least one C. For instance, in the illustrative example of a set having three members, the conjunctive phrases "at least one of A, B, and C" and "at least one of A, B and C" refer to any of the following sets: {A}, {B}, {C}, {A, B}, {A, C}, {B, C}, {A, B, C}, and, if not contradicted explicitly or by context, any set having {A}, {B}, and/or {C} as a subset (e.g., sets with multiple "A"). Thus, such conjunctive language is not generally intended to imply that certain embodiments require at least one of A, at least one of B and at least one of C each to be present. Similarly, phrases such as "at least one of A, B, or C" and "at least one of A, B or C" refer to the same as "at least one of A, B, and C" and "at least one of A, B and C" refer to any of the following sets: {A}, {B}, {C}, {A, B}, {A, C}, {B, C}, {A, B, C}, unless differing meaning is explicitly stated or clear from context. In addition, unless otherwise noted or contradicted by context, the term "plurality" indicates a state of being plural (e.g., "a plurality of items" indicates multiple items). The number of items in a plurality is at least two but can be more when so indicated either explicitly or by context.

Operations of processes described herein can be performed in any suitable order unless otherwise indicated herein or otherwise clearly contradicted by context. In an embodiment, a process such as those processes described herein (or variations and/or combinations thereof) is performed under the control of one or more computer systems configured with executable instructions and is implemented as code (e.g., executable instructions, one or more computer programs or one or more applications) executing collectively on one or more processors, by hardware or combinations thereof. In an embodiment, the code is stored on a computer-readable storage medium, for example, in the form of a computer program comprising a plurality of instructions executable by one or more processors. In an embodiment, a computer-readable storage medium is a non-transitory computer-readable storage medium that excludes transitory signals (e.g., a propagating transient electric or electromagnetic transmission) but includes non-transitory data storage circuitry (e.g., buffers, cache, and queues) within transceivers of transitory signals. In an embodiment, code (e.g., executable code or source code) is stored on a set of one or more non-transitory computer-readable storage media having stored thereon executable instructions that, when executed (i.e., as a result of being executed) by one or more processors of a computer system, cause the computer system to perform operations described herein. The set of non-transitory computer-readable storage media, in an embodiment, comprises multiple non-transitory computer-readable storage media, and one or more of individual non-transitory storage media of the multiple non-transitory computer-readable storage media lack all of the code while the multiple non-transitory computer-readable storage media collectively store all of the code. In an embodiment, the executable instructions are executed such that different instructions are executed by different processors—for example, in an embodiment, a non-transitory computer-readable storage medium stores instructions and a main CPU executes some of the instructions while a graphics processor unit executes other instructions. In another embodiment, different components of a computer system have separate processors and different processors execute different subsets of the instructions.

Accordingly, in an embodiment, computer systems are configured to implement one or more services that singly or collectively perform operations of processes described herein, and such computer systems are configured with applicable hardware and/or software that enable the performance of the operations. Further, a computer system, in an embodiment of the present disclosure, is a single device and, in another embodiment, is a distributed computer system comprising multiple devices that operate differently such that the distributed computer system performs the operations described herein and such that a single device does not perform all operations.

The use of any and all examples or exemplary language (e.g., "such as") provided herein is intended merely to better illuminate embodiments of the invention and does not pose a limitation on the scope of the invention unless otherwise claimed. No language in the specification should be construed as indicating any non-claimed element as essential to the practice of the invention.

Embodiments of this disclosure are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references including publications, patent applications, and patents cited herein are hereby incorporated by reference to the same extent as if each reference were individually and specifically indicated to be incorporated by reference and were set forth in its entirety herein.

What is claimed is:

1. A fitness system comprising:
   a rowing machine
   a processor in communication with the rowing machine; and
   a memory that stores computer-executable instructions that, as a result of being executed by the one or more processors, cause the fitness system to:
      obtain performance metrics corresponding to a series of workout sessions performed by a user using the rowing machine, each workout session of the series of workout sessions comprising a plurality of intervals corresponding to one of a number of different intensity levels;
      compare the performance metrics over at least a subset of the plurality of intervals of at least two of the workout sessions of the series of workout sessions with a prescribed performance of the corresponding interval within the at least two workout sessions to generate interval comparisons;
      categorize individual interval comparisons of the interval comparisons as relating to one of a sprint fitness interval corresponding to a shorter duration or higher intensity or an endurance fitness interval corresponding to a longer duration or a lower intensity based on attributes of the interval that is the subject of the individual interval comparison; and
      modify at least one of a length or an intensity level of at least one future interval of a future workout session based on the interval comparisons and based on whether the at least one future interval corresponds to a sprint fitness interval or an endurance fitness interval.

2. The fitness system of claim 1, wherein the computer-executable instructions that cause the fitness system to modify the at least one of a length or intensity level of the at least one future interval further include instructions that further cause the fitness system to:
   determine a sprint growth score based on the user's performance in sprint fitness intervals of the subset of intervals;
   determine an endurance growth score based on the user's performance in endurance fitness intervals of the subset of intervals; and
   adjust at least one of the length or the intensity level of the at least one future interval based on at least one of sprint growth score or the endurance growth score.

3. The fitness system of claim 2, wherein the computer-executable instructions that cause the fitness system to determine the sprint growth score and the endurance growth score further include instructions that further cause the system to:
   adjust at least one of the sprint growth score or the endurance growth score based on user fatigue.

4. The fitness system of claim 3, wherein user fatigue comprises at least one of mesocycle fatigue, intra-session fatigue based on at least one of intensity or length of the interval, or session fatigue based on an overall intensity of the workout.

5. A computer implemented method comprising:
   obtaining performance metrics from at least two workout sessions performed by a user using exercise equipment, each workout session of the at least two workout sessions comprising a plurality of intervals corresponding to one of a number of different intensity levels;
   comparing the performance metrics over at least a subset of the plurality of intervals of the at least two of the workout sessions with a prescribed performance of the corresponding interval to generate interval comparisons; and
   modifying at least one of a length or an intensity level of at least one interval of a future workout session based on the interval comparisons.

6. The computer-implemented method of claim 5, further comprising:
   categorizing individual intervals of the subset of intervals into one of a sprint interval or an endurance interval based on attributes of the individual intervals, wherein modifying at least one of the length or the intensity level of at least one interval is further based on whether individual intervals are categorized as a sprint interval or an endurance interval.

7. The computer-implemented method of claim 5, further comprising:
   determining a sprint growth score based on interval comparisons corresponding to sprint intervals;
   determining an endurance growth score based on interval comparisons corresponding to endurance intervals;
   modifying at least one of the length or the intensity level of at least one sprint interval of a future workout session based on the sprint growth score; and
   modifying at least one of the length or the intensity level of at least one endurance interval of a future workout session based on the endurance growth score.

8. The computer-implemented method of claim 7, further comprising:
   categorizing individual intervals of the subset of intervals into one of an aerobic interval, an anaerobic-alactic interval, and an anaerobic-lactic interval based on attributes of the individual intervals, wherein modifying at least one of the length or the intensity level of at least one interval is further based on whether individual intervals are categorized as an aerobic interval, an anaerobic-alactic interval, and an anaerobic-lactic interval.

9. The computer-implemented method of claim 5, wherein the performance metrics comprise at least one of output power or biometric data recorded by the exercise equipment for individual intervals of the plurality of intervals, and wherein the prescribed performance comprises at least one of a prescribed output power or prescribed biometric data for a corresponding individual interval of the plurality of intervals.

10. The computer-implemented method of claim 5, wherein comparing the performance metrics over at least the subset of the plurality of intervals with the prescribed performance of the corresponding interval to generate interval comparisons is performed for individual intervals of the subset of intervals.

11. The computer-implemented method of claim 5, further comprising:
   determining a fitness profile for the user based the performance metrics from at least one workout session performed by the user using exercise equipment, wherein the prescribed performance of the plurality of intervals of the at least two workout sessions are determined based on the fitness profile.

12. The computer-implemented method of claim 11, wherein the fitness profile comprises a power output function, the method further comprising:
   modifying the power output function based on the interval comparisons.

13. The computer-implemented method of claim 5, wherein modifying at least one of the length or the intensity level of at least one interval of the future workout session is further based on a fatigue metric corresponding to at least one of the at least two workouts.

14. The computer-implemented method of claim 5, wherein modifying at least one of the length or the intensity level of at least one interval of the future workout session is further based on a time period between the at least two workout sessions.

15. The computer-implemented method of claim 5, wherein modifying at least one of the length or the intensity level of at least one interval of the future workout session is further based on an average heart rate of the user recorded during at least one of the at least two workout sessions.

16. The computer-implemented method of claim 5, further comprising;
   representing a current user output in a graphical user interface, the graphical user interface comprising a number of areas corresponding to a number of different intensity zones, wherein the number of different intensity zones are mapped to different indicators of speed.

17. The computer-implemented method of claim 16, wherein the number of areas each comprise a first sized area, wherein individual zones of the number of different intensity zones span different sized ranges of intensity, and wherein representing the current user output comprises mapping an output to a location within one of the number of areas.

18. A non-transitory computer-readable storage medium storing thereon executable instructions that, as a result of being executed by one or more processors of a computer system, cause the computer system to at least:
   obtain performance data resulting from performance of a fitness test using exercise equipment by a user;
   determine a number and power output ranges of a plurality of intensity zones based on the obtained performance data;
   visually represent the plurality of intensity zones in a graphical user interface, wherein each of the plurality of intensity zones corresponds to an equal sized area in the graphical user interface independent of a duration of performance data of the user's use of the exercise equipment in the individual intensity zones; and
   map performance data of the user's use of the exercise equipment at a location within the equal sized area of the corresponding intensity zone, the location determined based on a relative intensity compared to the range of the corresponding intensity level.

19. The non-transitory computer-readable storage medium of claim 18, wherein a span of the power output ranges of individual intensity zones of the plurality of intensity zones are different.

20. The non-transitory computer-readable storage medium of claim 18, wherein the instructions further comprise instructions that, as a result of being executed by the one or more processors, cause the computer system to:
   translate intensity values to speed values; and
   represent the plurality of intensity zones as speed zones.

21. The non-transitory computer-readable storage medium of claim 18, wherein the instructions further comprise instructions that, as a result of being executed by the one or more processors, cause the computer system to:
   obtain second performance data resulting from performance of a workout using the exercise equipment by the user; and
   adjust the power output ranges of at least one of the plurality of intensity zones based on the second performance data.

* * * * *